US011339051B2

(12) United States Patent
Imamura et al.

(10) Patent No.: US 11,339,051 B2
(45) Date of Patent: May 24, 2022

(54) OZONE GENERATING DEVICE, AIR CONDITIONING DEVICE, AND VEHICLE

(71) Applicant: Ushio Denki Kabushiki Kaisha, Tokyo (JP)

(72) Inventors: Atsushi Imamura, Tokyo (JP); Kazuhiro Goto, Tokyo (JP)

(73) Assignee: USHIO DENKI KABUSHIKI KAISHA, Tokyo (JP)

( * ) Notice: Subject to any disclaimer, the term of this patent is extended or adjusted under 35 U.S.C. 154(b) by 128 days.

(21) Appl. No.: 16/489,841

(22) PCT Filed: Mar. 8, 2019

(86) PCT No.: PCT/JP2019/009275
§ 371 (c)(1),
(2) Date: Aug. 29, 2019

(87) PCT Pub. No.: WO2019/193922
PCT Pub. Date: Oct. 10, 2019

(65) Prior Publication Data
US 2021/0009416 A1    Jan. 14, 2021

(30) Foreign Application Priority Data

Apr. 2, 2018   (JP) .............................. JP2018-070759
Apr. 2, 2018   (JP) .............................. JP2018-070761

(51) Int. Cl.
*C01B 13/11*    (2006.01)
*B60H 3/00*     (2006.01)
*H01J 65/00*    (2006.01)

(52) U.S. Cl.
CPC ............ *C01B 13/11* (2013.01); *B60H 3/0078* (2013.01); *C01B 2201/14* (2013.01); *C01B 2201/22* (2013.01); *H01J 65/00* (2013.01)

(58) Field of Classification Search
CPC . C01B 13/11; C01B 2201/14; C01B 2201/22; C01B 13/10; B60H 3/0078;
(Continued)

(56) References Cited

U.S. PATENT DOCUMENTS

| 5,869,931 A | * | 2/1999 | Terada | H01J 61/70 313/607 |
| 2011/0068678 A1 | * | 3/2011 | Watanabe | H01J 65/046 313/486 |
| 2018/0230011 A1 | * | 8/2018 | Naito | A61L 9/12 |

FOREIGN PATENT DOCUMENTS

| JP | 2002-103959 A | | 4/2002 |
| WO | WO2017/033727 | * | 3/2017 |
| WO | 2017-082380 A1 | | 5/2017 |

OTHER PUBLICATIONS

Notification of Transmittal of Translation of the International Preliminary Report on Patentability and Translation of Written Opinion of the International Searching Authority; PCT/JP2019/009275; dated Oct. 15, 2020.
(Continued)

*Primary Examiner* — Xiuyu Tai
(74) *Attorney, Agent, or Firm* — Studebaker & Brackett PC

(57) ABSTRACT

An ozone generating device including an excimer lamp having an arc tube containing a luminescent gas, a first electrode, and a second electrode. The arc tube has a first end portion and a second end portion, a first diameter-reduced portion provided continuously from the first end portion, a diameter of which decreases as a distance from the first end portion increases, and a second diameter-reduced portion provided continuously from the second end portion, a diameter of which decreases as a distance from the second end portion increases, the first electrode is provided for an outer periphery surface of the first end portion, the second elec-
(Continued)

trode is provided for an outer periphery surface of the second end portion, the arc tube is fixed via the cylindrical portion, and the first electrode is not provided over the first diameter-reduced portion, and/or the second electrode is not provided over the second diameter-reduced portion.

14 Claims, 12 Drawing Sheets

(58) Field of Classification Search
CPC .......... H01J 65/00; H01J 61/368; H01J 61/06; H01J 9/247; H01J 61/48; H01J 65/042; H01J 61/35; H01J 65/04; H01J 9/20; H01J 2209/015; H01J 63/04; H01J 1/62; H01J 61/70; H01J 61/52; A61L 2/26; A61L 9/046; A61L 9/12; A61L 2/202; A61L 9/20

See application file for complete search history.

(56) References Cited

OTHER PUBLICATIONS

The extended European search report issued by the European Patent Office dated Apr. 28, 2020, which corresponds to European Patent Application No. 19780618.5-1106 and is related to U.S. Appl. No. 16/489,841.

International Search Report issued in PCT/JP2019/009275; dated Apr. 2, 2019.

* cited by examiner

OZONE GENERATING DEVICE, AIR CONDITIONING DEVICE, AND VEHICLE

TECHNICAL FIELD

The present invention (first invention and second invention) relates to an ozone generating device, an air conditioning device, and a vehicle.

BACKGROUND ART

Conventionally, an ozone generating device using an ultraviolet lamp has been known. Known examples of the ultraviolet lamp for generating ozone include a mercury lamp and an excimer lamp (e.g., xenon excimer lamp).

Patent Document 1 discloses a sterilization device for an automotive air conditioner, which sterilization device includes an ozone generator on a downstream side of an evaporator (evaporating device), and describes that with this, breeding of bacteria over a surface of the evaporator is prevented.

PRIOR ART DOCUMENT

Patent Document

Patent Document 1: JP-A-2002-103959

SUMMARY OF THE INVENTION

Problems to be Solved by the Invention

<First Problem>

However, when the ozone generating device is placed at a portion that is easily oscillated (e.g., on a vehicle), it is likely that the ultraviolet lamp can become broken. As the ultraviolet lamp is configured to enclose a luminescent gas, it has a portion, in manufacturing, at which a stress is easily concentrated. Therefore, breakage is more likely to occur especially at a portion at which a stress is easily concentrated due to oscillation.

A first invention is made in view of the above problem, and an object of the first invention is to provide an ozone generating device capable of reducing risks of breakage due to oscillation and the like. Further, the first invention is to provide an air conditioning device having such an ozone generating device. Moreover, the first invention is to provide a vehicle having such an air conditioning device.

<Second Problem>

In recent years, mercury-free is recommended due to environmental consciousness. Further, an excimer lamp (especially a xenon excimer lamp that emits light of a wavelength 172 nm) has a higher ozone generation efficiency as compared to a mercury lamp that emits light of a wavelength 185 nm and a wavelength 254 nm.

However, structurally, an electrode of the excimer lamp is exposed over an outer periphery surface of an arc tube. Therefore, a problem that ozone generated by the excimer lamp produces oxidation of the electrode could occur. Such a problem can become noticeable especially when an excimer lamp that emits light of a wavelength 172 nm is used in order to improve the ozone generation efficiency, as an amount of generation of ozone increases. Further, when a large amount of moisture is contained within a use environment (e.g., when installation is carried out within an air conditioning device), oxidation of the electrode can become further noticeable due to presence of both moisture and ozone.

It should be noted that Patent Document 1 describes that an ultraviolet lamp is used as an ozone generator, but its specific configuration is not described. Assuming that a mercury lamp is used, there is a room for improvement in terms of mercury free. Alternatively, assuming that an excimer lamp is used, there is a problem of oxidation of electrode due to ozone as described above.

A second invention is made in view of the above problem, and an object of the second invention is to provide an ozone generating device capable of reducing deterioration of an electrode by ozone generated using an excimer lamp. Further, the second invention is to provide an air conditioning device having such an ozone generating device. Moreover, the second invention is to provide a vehicle having such an air conditioning device.

Means for Solving the Problems

<First Invention>

In order to solve the first problem, the inventors of the present invention find out that the first problem can be solved by employing the following configuration, and thus accomplish the first invention.

Specifically, an ozone generating device according to the first invention includes:

an excimer lamp having an arc tube in which a luminescent gas is enclosed, a first electrode, and a second electrode, wherein the arc tube includes a cylindrical portion having a first end portion and a second end portion, a first diameter-reduced portion provided continuously from the first end portion, a diameter of which decreases as a distance from the first end portion increases, and a second diameter-reduced portion provided continuously from the second end portion, a diameter of which decreases as a distance from the second end portion increases, the first electrode is provided for an outer periphery surface of the first end portion, the second electrode is provided for an outer periphery surface of the second end portion, the arc tube is fixed via the cylindrical portion, and the first electrode is not provided over the first diameter-reduced portion, and/or the second electrode is not provided over the second diameter-reduced portion.

At the first diameter-reduced portion and the second diameter-reduced portion, a stress is easily concentrated due to their shapes as compared to the cylindrical portion. Therefore, in the first invention, the arc tube is fixed by the cylindrical portion. With this, it is possible to reduce risks of breakage due to oscillation and the like.

Further, due to a difference between thermal expansion rates of the arc tube and the electrode (the first electrode and the second electrode), a stress is produced at a contact portion between the arc tube and the electrode. Further, when the arc tube is fixed by the cylindrical portion via the first electrode and the second electrode, a portion of the arc tube in contact with the first electrode and the second electrode is a portion to which an impact such as oscillation is easily transmitted. Therefore, in the first invention, one of three configurations are employed: (1) the first electrode is not provided over the first diameter-reduced portion, (2) the second electrode is not provided over the second diameter-reduced portion, and (3) the first electrode is not provided over the first diameter-reduced portion and the second electrode is not provided over the second diameter-reduced portion. With this, a configuration is provided in which a stress due to a difference between thermal expansion rates and an impact such as oscillation may not be easily transmitted to the first diameter-reduced portion, and/or the second diameter-reduced portion. As a result, it is possible to reduce risks of breakage due to oscillation and the like.

Further, with the excimer lamp, an electrode is not provided within its arc tube, but only on the outer periphery surface. Therefore, the excimer lamp may be easily manufactured only by enclosing the luminescent gas within the arc tube and then providing the electrode for the outer periphery surface.

Further, as an electrode is not provided within the arc tube, and wiring electrically connecting an interior with an exterior of the arc tube is not necessary, there is no member that penetrate a wall surface of the arc tube. Accordingly, it is possible to maintain high reliability of the excimer lamp. Specifically, when there is wiring electrically connecting an interior with an exterior of the arc tube, and when exposed to high temperatures, for example, a problem such as breakage may occur due to a difference between thermal expansion rates of the arc tube and the wiring. However, according to the excimer lamp of the first invention, this problem may not occur, as there is no member that penetrate a wall surface of the arc tube.

Further, with the excimer lamp, an electrode is not provided within its arc tube, but only on the outer periphery surface. Therefore, it is possible to manufacture the excimer lamp in small sizes. As a result, it is possible to manufacture an excimer lamp that can be easily placed in a space that is limited.

In the above configuration, it is preferable that the first electrode is not provided over the first diameter-reduced portion, and the second electrode is not provided over the second diameter-reduced portion.

By employing the configuration in which the first electrode is not provided over the first diameter-reduced portion, and the second electrode is not provided over the second diameter-reduced portion, a configuration is provided in which a stress due to a difference between thermal expansion rates and an impact such as oscillation may not be easily transmitted to both of the first diameter-reduced portion and the second diameter-reduced portion. As a result, it is possible to further reduce risks of breakage due to oscillation and the like.

In the above configuration, it is preferable to further provide: a first protecting portion provided so as to cover the first electrode; and a second protecting portion provided so as to cover the second electrode, wherein the first protecting portion and the second protecting portion are apart from each other.

When the first electrode is covered by the first protecting portion, the second electrode is covered by the second protecting portion, and the first protecting portion and the second protecting portion are apart from each other, the first electrode and the second electrode are covered by the protecting portion (the first protecting portion and the second protecting portion), and the tube-axial direction central portion of the arc tube is exposed. With such a configuration, without shielding light emitted from the arc tube largely, it is possible to cover the electrodes (the first electrode and the second electrode) by the protecting portion (the first protecting portion and the second protecting portion). With this, it is possible to prevent the electrodes from being deteriorated by ozone while maintaining the ozone generation efficiency high. Further, it is possible to prevent moisture present in a use environment from reaching an electrode portion.

In the above configuration, it is preferable that a main emission wavelength of the excimer lamp is 200 nm or lower.

If the main emission wavelength is 200 nm or lower, as compared to a case in which the main emission wavelength is 200 nm or higher, the emission is easily absorbed to the arc tube, and the arc tube becomes easily deformed. However, according to the above configuration, the electrodes (the first electrode and/or the second electrode) are not provided over the diameter-reduced portions (the first diameter-reduced portion and/or the second diameter-reduced portion) at which a stress is easily concentrated. As a result, it is possible to further reduce risks of breakage.

Further, it is advantageous when the excimer lamp whose main emission wavelength is 200 nm or lower if the main emission wavelength of the excimer lamp is 200 nm or lower, as an amount of generated ozone becomes large.

It should be noted that in this specification, the main emission wavelength means a peak wavelength in a wavelength range of a wavelength 300 nm or lower. If a peak is one in an emission spectrum of a wavelength 300 nm or lower, this peak wavelength referred to as a main emission wavelength, and if there are more than one peak, a peak wavelength whose relative emission intensity is highest is referred to as a main emission wavelength.

In the above configuration, it is preferable that the first protecting portion and the second protecting portion include openings corresponding to a tube diameter of the arc tube.

When the opening corresponding to the tube diameter of the arc tube is provided for the first protecting portion and the second protecting portion, the excimer lamp may be held by providing the arc tube in the opening.

In the above configuration, it is preferable that a first light shielding member for shielding light emitted from the arc tube is provided between the opening and the arc tube.

As the first light shielding member is provided, light emitted from the arc tube is prevented from reaching the opening portion of the protecting portion (the first protecting portion and the second protecting portion), and it is possible to suppress deterioration of a portion of the opening due to the light.

In the above configuration, it is preferable that a tapered portion is provided around the opening of the first protecting portion and around the opening of the second protecting portion.

When the tapered portion is provided around the opening of the first protecting portion and the opening of the second protecting portion, ozone may not easily reach inside of the protecting portion (inside of the first protecting portion and inside of the second protecting portion). Further, the arc tube may be held by a surface around opening including the tapered portion, and breakage may be reduced.

In the above configuration, it is preferable to further provide a connecting portion that connects the first protecting portion with the second protecting portion, wherein, the first protecting portion, the connecting portion, and the second protecting portion are provided integrally as the casing.

If the first protecting portion, the connecting portion, and the second protecting portion are integrally formed into the casing, it is possible to hold the excimer lamp stably by the first protecting portion and the second protecting portion.

In the above configuration, it is preferable that the arc tube and the connecting portion are apart from each other.

When the arc tube and the connecting portion are apart from each other, light emitted from the arc tube can be efficiently irradiated to oxygen from all direction of the arc tube, and thus it is possible to increase an amount of generated ozone. Further, when the arc tube and the connecting portion are apart from each other, it is possible to prevent the connecting portion from being deteriorated by light emitted from the arc tube.

In the above configuration, it is preferable that a second light shielding member provided between an end surface of the arc tube and an inner wall of the first protecting portion facing against the end surface of the arc tube, and between the end surface of the arc tube and the inner wall of the second protecting portion facing against the end surface of the arc tube, the second light shielding member preventing light emitted from the end surface of the arc tube from reaching the inner wall.

If the second light shielding member is provided, it is possible to shield light emitted from the end surface of the arc tube to the inner wall, and to prevent deterioration of the inner wall (the first protecting portion and the second protecting portion) due to the light.

In the above configuration, it is preferable that the ozone generating device is for vehicle applications.

As risks of breakage of the arc tube due to oscillation and the like is reduced, the ozone generating device may be advantageously used for a vehicle on which oscillation and the like can frequently occur. Further, as the ozone generating device can be easily made small, the ozone generating device is advantageously used for a vehicle with a limited space.

Further, an air conditioning device according to the first invention includes:

a flow channel;

an evaporating device provided within the flow channel;

an ozone generating device described above, provided within the flow channel; and an air blower provided on an upstream side of the evaporating device.

According to the above configuration, bacteria and the like generated over a surface of the evaporating device may be sterilized by ozone generated by the ozone generating device. With this, it is possible to suppress an offensive smell and the like due to bacteria and the like. Further, as risks of breakage of the arc tube due to oscillation and the like is reduced, the ozone generating device may be advantageously used for air conditioning devices having a member such as an air blower with which oscillation and the like can occur.

In the above configuration, it is preferable that the ozone generating device is positioned such that a tube-axial direction of the arc tube and an air-blowing direction intersect each other.

When the ozone generating device is provided such that the tube-axial direction of the arc tube and the air-blowing direction intersect each other, it is possible to efficiently treat a larger amount of oxygen by light emitted from the arc tube.

Further, a vehicle according to the first invention includes the air conditioning device.

According to the ozone generating device, as risks of breakage of the arc tube due to oscillation and the like is reduced, risks of breakage of the arc tube due to oscillation and the like of the air conditioning device having the ozone generating device is also reduced. As a result, the air conditioning device may be advantageously mounted on a vehicle on which oscillation and the like can frequently occur. Further, as the ozone generating device can be easily made small, the air conditioning device having the ozone generating device can also be made small. As a result, the air conditioning device is advantageously mounted on a vehicle with a limited space.

In the above configuration, it is preferable that the ozone generating device is positioned such that a direction perpendicular to a floor surface of the vehicle matches a tube-axial direction of the arc tube.

When the ozone generating device is positioned such that the direction perpendicular to the floor surface of the vehicle matches the tube-axial direction of the arc tube, it is possible to suppress breakage of the arc tube due to up-down vibration (vertical vibration) when the vehicle travels.

Hereinbefore, the first invention has been described.

<Second Invention>

In order to solve the second problem, the inventors of the present invention find out that the second problem can be solved by employing the following configuration, and thus accomplish the second invention.

Specifically, an ozone generating device according to the second invention includes:

an excimer lamp having an arc tube in which a luminescent gas is enclosed, and electrodes provided for an outer periphery surface at both end portions of the arc tube in the tube-axial direction; and a protecting portion provided so as to cover the electrode.

According to the second invention, as the excimer lamp, an excimer lamp having the electrodes provided for the outer periphery surface at the both end portions of the arc tube in the tube-axial direction. Then, the electrodes are covered by the protecting portions. As a result, portions covered by the protecting portions are the both end portions of the arc tube in the tube-axial direction, and a tube-axial direction central portion of the arc tube is exposed. With such a configuration, without shielding light emitted from the arc tube largely, it is possible to cover the electrodes by the protecting portions. With this, it is possible to prevent the electrodes from being deteriorated by ozone while maintaining the ozone generation efficiency high. Further, it is possible to prevent moisture present in a use environment from reaching an electrode portion.

Further, with the excimer lamp, an electrode is not provided within its arc tube, but only on the outer periphery surface. Therefore, the excimer lamp may be easily manufactured only by enclosing the luminescent gas within the arc tube and then providing the electrode for the outer periphery surface.

Further, as an electrode is not provided within the arc tube, and wiring electrically connecting an interior with an exterior of the arc tube is not necessary, there is no member that penetrate a wall surface of the arc tube. Accordingly, it is possible to maintain high reliability of the excimer lamp. Specifically, when there is wiring electrically connecting an interior with an exterior of the arc tube, and when exposed to high temperatures, for example, a problem such as breakage may occur due to a difference between thermal expansion rates of the arc tube and the wiring. However, according to the excimer lamp of the second invention, this problem may not occur, as there is no member that penetrate a wall surface of the arc tube.

Further, with the excimer lamp, an electrode is not provided within its arc tube, but only on the outer periphery surface. Therefore, it is possible to manufacture the excimer lamp in small sizes. As a result, it is possible to manufacture an excimer lamp that can be easily placed in a space that is limited.

In the above configuration, it is preferable that the protecting portion includes an opening corresponding to a tube diameter of the arc tube.

When the opening corresponding to the tube diameter of the arc tube is provided for the protecting portion, the excimer lamp may be held by providing the arc tube in the opening.

In the above configuration, it is preferable that a first light shielding member for shielding light emitted from the arc tube is provided between the opening and the arc tube.

As the first light shielding member is provided, light emitted from the arc tube is prevented from reaching the opening portion of the protecting portion, and it is possible to suppress deterioration of a portion of the opening due to the light.

In the above configuration, it is preferable that a tapered portion is provided around the opening of the protecting portion.

When the tapered portion is provided around the opening of the protecting portion, ozone may not easily reach the protecting portion. Further, the arc tube may be held by a surface around opening including the tapered portion, and breakage may be reduced.

In the above configuration, it is preferable that the protecting portion includes a first protecting portion provided so as to cover one of the electrodes, and a second protecting portion provided so as to cover the other of the electrodes, a connecting portion that connects the first protecting portion with the second protecting portion is further provided, and the first protecting portion, the connecting portion, and the second protecting portion are provided integrally as a casing.

If the first protecting portion, the connecting portion, and the second protecting portion are integrally formed into the casing, it is possible to hold the excimer lamp stably by the first protecting portion and the second protecting portion.

In the above configuration, it is preferable that the arc tube and the connecting portion are apart from each other.

When the arc tube and the connecting portion are apart from each other, light emitted from the arc tube can be efficiently irradiated to oxygen from all direction of the arc tube, and thus it is possible to increase an amount of generated ozone. Further, when the arc tube and the connecting portion are apart from each other, it is possible to prevent the connecting portion from being deteriorated by light emitted from the arc tube.

In the above configuration, it is preferable that a second light shielding member provided between an end surface of the arc tube and an inner wall of the protecting portion facing against the end surface of the arc tube, the second light shielding member preventing light emitted from the end surface of the arc tube from reaching the inner wall.

If the second light shielding member is provided, it is possible to shield light emitted from the end surface of the arc tube, and to prevent deterioration of the inner wall (the protecting portion) due to the light.

In the above configuration, it is preferable that the ozone generating device is for vehicle applications.

As the ozone generating device can be easily made small, the ozone generating device is advantageously used for a vehicle with a limited space.

Further, an air conditioning device according to the second invention includes:

a flow channel;

an evaporating device provided within the flow channel;

an ozone generating device described above, provided within the flow channel; and an air blower provided on an upstream side of the evaporating device.

According to the above configuration, bacteria and the like generated over a surface of the evaporating device may be sterilized by ozone generated by the ozone generating device. With this, it is possible to suppress an offensive smell and the like due to bacteria and the like.

In the above configuration, it is preferable that the ozone generating device is positioned such that a tube-axial direction of the arc tube and an air-blowing direction intersect each other.

When the ozone generating device is provided such that the tube-axial direction of the arc tube and the air-blowing direction intersect each other, it is possible to efficiently irradiate light emitted from the arc tube to a larger amount of oxygen.

Further, a vehicle according to the second invention includes the air conditioning device.

As the ozone generating device can be easily made small, the air conditioning device having the ozone generating device can also be made small. As a result, the air conditioning device is advantageously mounted on a vehicle with a limited space.

In the above configuration, it is preferable that the ozone generating device is positioned such that a direction perpendicular to a floor surface of the vehicle matches a tube-axial direction of the arc tube.

When the ozone generating device is positioned such that the direction perpendicular to the floor surface of the vehicle matches the tube-axial direction of the arc tube, it is possible to suppress breakage of the arc tube due to up-down vibration (vertical vibration) when the vehicle travels.

Hereinbefore, the second invention has been described.

Effect of the Invention

According to the first invention, it is possible to provide an ozone generating device capable of reducing risks of breakage due to oscillation and the like. Further, it is possible to provide an air conditioning device having such an ozone generating device. Moreover, it is possible to provide a vehicle having such an air conditioning device.

According to the second invention, it is possible to provide an ozone generating device capable of reducing deterioration of an electrode by ozone generated using an excimer lamp. Further, it is possible to provide an air conditioning device having such an ozone generating device. Moreover, it is possible to provide a vehicle having such an air conditioning device.

MODE FOR CARRYING OUT THE INVENTION

Hereinafter, first of all, an ozone generating device according to one embodiment of the present invention (first invention, second invention) will be described with reference to the drawings.

It should be noted in the following description, when simply stating that "the present invention" without distinguishing between a "first invention" and a "second invention", this means both of the "first invention" and the "second invention".

First Embodiment

Figure 1:
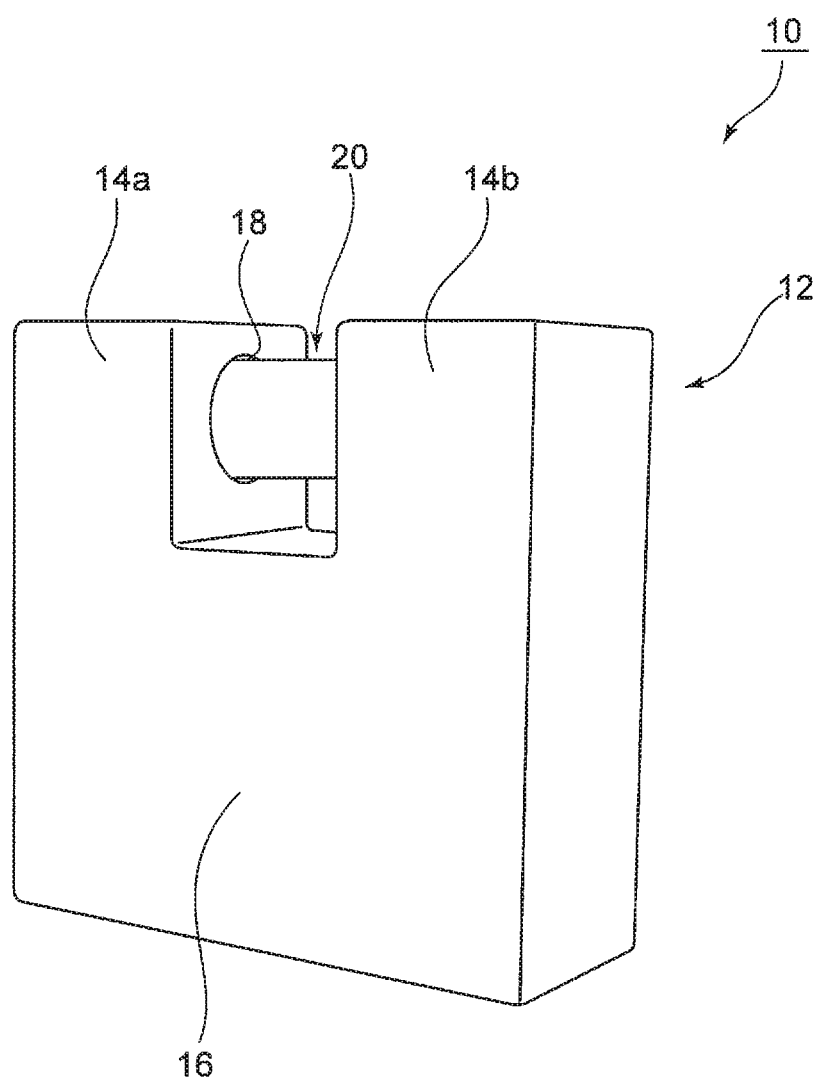
FIG. 1 is a perspective view schematically illustrating an ozone generating device according to a first embodiment.
Figure 2:
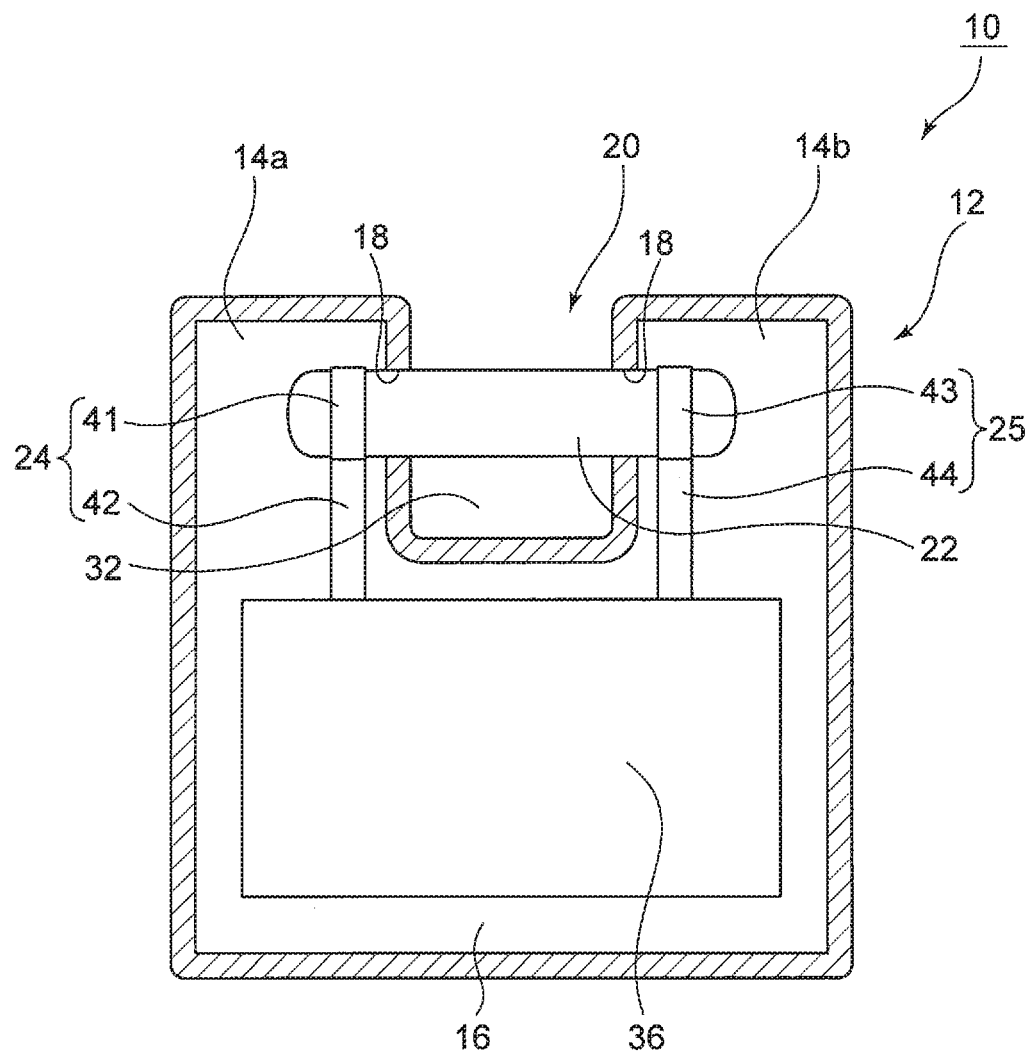
FIG. 2 is a front view of the ozone generating device shown in FIG. 1, with a front half of its casing removed for illustration.

FIG. 1 is a perspective view schematically illustrating an ozone generating device according to the first embodiment. FIG. 2 is a front view of the ozone generating device shown in FIG. 1, with a front half of its casing removed for illustration.

As shown in FIG. 1 and FIG. 2, an ozone generating device 10 includes a casing 12 and an excimer lamp 20.

Figure 3:
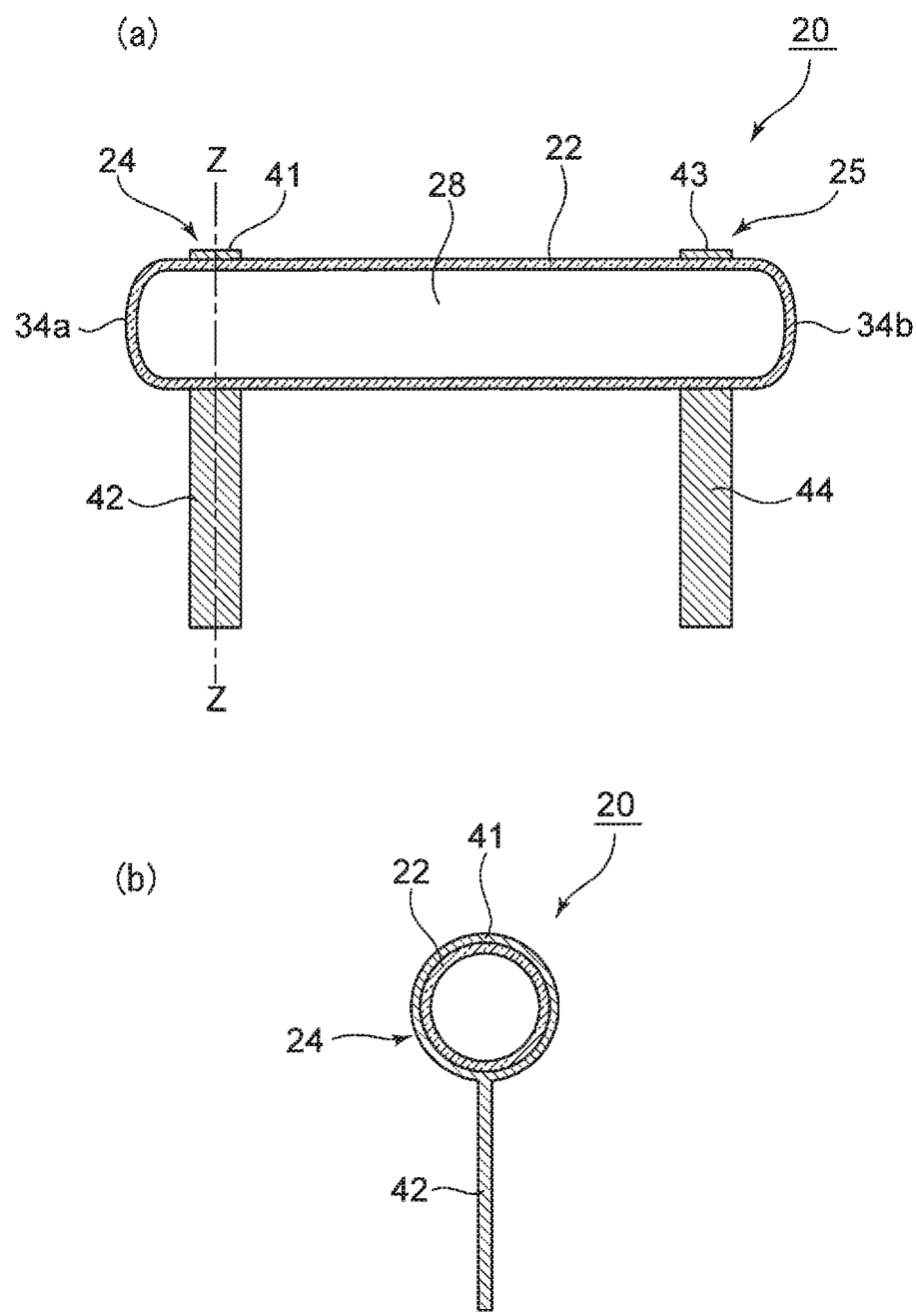
FIG. 3(a) is a sectional view of an excimer lamp provided for the ozone generating device shown in FIG. 1 in a tube-axial direction.
FIG. 3(b) is a sectional view of this excimer lamp taken along line Z-Z.
Figure 4:
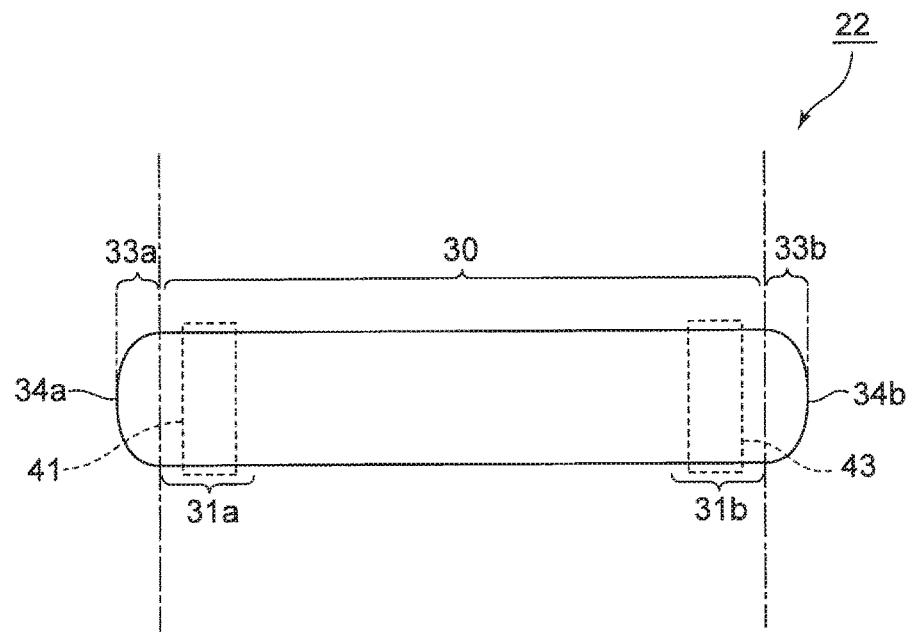
FIG. 4 is a front view of an arc tube provided for the excimer lamp shown in FIG. 3(a).

FIG. 3(a) is a sectional view of an excimer lamp provided for the ozone generating device shown in FIG. 1 in a tube-axial direction, and FIG. 3(b) is a sectional view of this excimer lamp taken along line Z-Z. FIG. 4 is a front view of an arc tube provided for the excimer lamp shown in FIG. 3(a).

The excimer lamp 20 includes an arc tube 22 in which a luminescent gas is contained, a first electrode 24, and a second electrode 25.

The arc tube 22 includes a cylindrical portion 30, a first diameter-reduced portion 33a, and a second diameter-reduced portion 33b (cf. FIG. 4).

The cylindrical portion 30 is in a hollow cylindrical shape having a doughnut-shaped cross section. The cylindrical portion 30 includes a first end portion 31a on one end (left end in FIG. 4), and a second end portion 31b on the other end (right end in FIG. 4).

The first diameter-reduced portion 33a is provided continuously from the first end portion 31a toward a direction away from the first end portion 31a (leftward in FIG. 4). A diameter of the first diameter-reduced portion 33a decreases as a distance from the first end portion 31a increases, and closes at an end surface 34a.

The second diameter-reduced portion 33b is provided continuously from the second end portion 31b toward a direction away from the second end portion 31b (rightward in FIG. 4). A diameter of the second diameter-reduced portion 33b decreases as a distance from the second end portion 31b increases, and closes at an end surface 34b.

Here, the shapes of the end surface 34a and the end surface 34b are not particularly limited as long as the ends are closed, and may be curved surfaces or flat surfaces. Further, projections and the like produced when closing the ends may present.

It should be noted that while this embodiment describes a case in which the excimer lamp 20 is an excimer lamp utilizing dielectric-barrier discharge, the excimer lamp of the present invention may be any lamp that emits light from excimer, and the present invention is not limited to the case in which dielectric-barrier discharge is utilized.

While a material of the arc tube 22 is not particularly limited, it is preferable to use a material that passes ultraviolet light, such as quartz glass, for example.

A type of the luminescent gas is not particularly limited, as long as the gas is able to emit light of wavelength that allows generation of ozone when irradiated to oxygen. Examples of the luminescent gas include xenon (output wavelength: 172 nm), krypton chloride (output wavelength: 222 nm), and krypton bromide (output wavelength: 207 nm).

One example of an enclosure method of the luminescent gas is as follows. First, a hollow cylindrical tube having a doughnut-shaped cross section and both ends are open is prepared. Then, one end of the tube is closed by thermofusion. With this, a diameter-reduced portion is achieved. Next, an interior of the tube whose one end is closed is depressurized (preferably, vacuumized), and a luminescent gas is introduced within the tube. Thereafter, the other end of the tube is quickly closed by thermofusion. In this manner, the luminescent gas may be enclosed within the arc tube 22.

The first electrode 24 includes an electrode main body 41 provided on an outer periphery surface of the first end portion 31a, and an extending portion 42 extending from the electrode main body 41. The electrode main body 41 and the extending portion 42 are made of the same material in a continuous manner.

The extending portion 42 extends from the electrode main body 41 in a direction away from the outer periphery surface of the first end portion 31a. The extending portion 42 is electrically connected to an electronic component 36 that will be later described.

The second electrode 25 includes an electrode main body 43 provided on an outer periphery surface of the second end portion 31b, and an extending portion 44 extending from the electrode main body 43. The electrode main body 43 and the extending portion 44 are made of the same material in a continuous manner.

The extending portion 44 extends from the electrode main body 43 in a direction away from the outer periphery surface of the second end portion 31b. The extending portion 44 is electrically connected to the electronic component 36 that will be later described.

While the shapes of the electrode main body 41 and the electrode main body 43 are not particularly limited, a cylindrical shape is preferable as in this embodiment. This is because it is possible to perform dielectric-barrier discharge more advantageously if the shape is cylindrical. Different examples of the shape of the electrode main body include a shape having a C-shaped cross section and a coiled shape.

It is more preferable that an area that the electrode main body 41 and the electrode main body 43 cover an outer periphery surface of the arc tube 22 is larger, in terms of startability. Therefore, it is preferable that the shape is cylindrical as in this embodiment.

In this embodiment, the electrode main body 41 is not provided over the first diameter-reduced portion 33a. In other words, the first electrode 24 is only in contact with the cylindrical portion 30 of the arc tube 22, and not with the first diameter-reduced portion 33a. Further, the electrode main body 43 is not provided over the second diameter-reduced portion 33b. In other words, the second electrode 25 is only in contact with the cylindrical portion 30 of the arc tube 22, and not with the second diameter-reduced portion 33b.

The materials, thicknesses, and the like of the extending portion 42 and the extending portion 44 are adjusted so that the extending portion 42 and the extending portion 44 are able to bear a weight of the arc tube 22 and stand on their own. In other words, the arc tube 22 is fixed to the electronic component 36 via the first electrode 24 and the second electrode 25.

The material of the first electrode 24 and the second electrode 25 is not particularly limited, but stainless steel and kanthal (iron-chromium alloy) are preferable in terms of an oxidation resistance and a thermal shock resistance at high temperatures.

According to the excimer lamp 20, when an alternating-current high voltage is applied between the first electrode 24 and the second electrode 25, dielectric-barrier discharge is induced in a space 28 within the arc tube 22. Then, this excites the luminescent gas to be in an excimer state, and when the gas resumes an original state (ground state) from the excimer state, a spectrum unique to excimer is emitted (excimer emission).

With the ozone generating device 10 according to this embodiment, the arc tube 22 is fixed via the first electrode 24 and the second electrode 25. Therefore, portions of the arc tube 22 at which the arc tube 22 is in contact with the first electrode 24 and the second electrode 25 are portions to which impact such as oscillation is easily transmitted. Here, at the first diameter-reduced portion 33a and the second diameter-reduced portion 33b, a stress is easily concentrated due to their shapes as compared to the cylindrical portion 30. Therefore, this embodiment employs a configuration in which the first electrode 24 is not provided over the first diameter-reduced portion 33a, and the second electrode 25 is not provided over the second diameter-reduced portion 33b. With this, a configuration is provided in which an impact such as oscillation may not easily transmitted to the first diameter-reduced portion 33a and the second diameter-reduced portion 33b. As a result, it is possible to reduce risks of breakage due to oscillation and the like.

Further, the cylindrical portion 30, the first diameter-reduced portion 33a, and the second diameter-reduced portion 33b are usually are made of the same material in a continuous manner, and the first diameter-reduced portion 33a and the second diameter-reduced portion 33b are closed by meltage. As the first diameter-reduced portion 33a and the second diameter-reduced portion 33b are closed by meltage, it is difficult to make a thickness of the first diameter-reduced portion 33a and a thickness of the second diameter-reduced portion 33b even due to reasons regarding manufacturing. Further, it is difficult to make a diameter of the diameter-reduced portions decreased evenly as the diameter-reduced portions become more distant from the end portions (the first end portion 31a and the second end portion 31b) of the cylindrical portion 30. Therefore, the first diameter-reduced portion 31a and the second diameter-reduced portion 31b, are portions at which a stress is concentrated particularly easily. However, as described above, this embodiment employs the configuration in which an impact such as oscillation is not easily transmitted to the first diameter-reduced portion 33a and the second diameter-reduced portion 33b. As a result, it is possible to further reduce risks of breakage due to oscillation and the like.

It is preferable that a main emission wavelength of the excimer lamp 20 is 200 nm or lower. Examples of a method for limiting the main emission wavelength of the excimer lamp 20 to be 200 nm or lower include a method of selecting the luminescent gas appropriately. It is advantageous if the main emission wavelength of the excimer lamp 20 is 200 nm or lower, as an amount of generated ozone becomes large. Further, if the main emission wavelength of the excimer lamp 20 is 200 nm or lower, as compared to a case in which the main emission wavelength is 200 nm or higher, the emission is easily absorbed to the arc tube 22, and the arc tube 22 becomes easily deformed. However, according to the ozone generating device 10 of this embodiment, the electrodes (the first electrode 24 and the second electrode 25) are not provided over the diameter-reduced portions (the first diameter-reduced portion 33a and the second diameter-reduced portion 33b) at which a stress is easily concentrated. As a result, it is possible to further reduce risks of breakage.

With the excimer lamp 20, an electrode is not provided within its arc tube, but only on the outer periphery surface. Therefore, the excimer lamp 20 may be easily manufactured only by enclosing the luminescent gas within the arc tube 22 and then providing the first electrode 24 and the second electrode 25.

Further, with the excimer lamp 20, an electrode is not provided within the arc tube, and wiring electrically connecting an interior with an exterior of the arc tube is not necessary. Therefore, there is no member that penetrate a wall surface of the arc tube 22. Accordingly, it is possible to maintain high reliability of the excimer lamp 20.

As described above, with the excimer lamp 20, an electrode is not provided within its arc tube, but only on the outer periphery surface. Therefore, it is possible to manufacture the excimer lamp 20 in small sizes. Because the excimer lamp 20 can be made easily in small sizes, dimensions of the excimer lamp 20 are as follows. An entire length in a tube-axial direction is preferably from 10 mm to 150 mm, more preferably from 10 mm to 100 mm, and further preferably from 10 mm to 50 mm. Further, a distance between the electrodes is preferably from 3 mm to 130 mm, more preferably from 3 mm to 80 mm, and further preferably from 3 mm to 30 mm. Here, the distance between the electrodes means a distance between portions of the electrodes that are closest to each other. Moreover, when the shape is cylindrical, an outer diameter is preferably from 3 mm to 20 mm, more preferably from 3 mm to 15 mm, and further preferably from 3 mm to 10 mm. Furthermore, a wall thickness of the arc tube 22 is preferably from 0.1 mm to 2 mm, more preferably from 0.1 mm to 1 mm, and further preferably from 0.1 mm to 0.5 mm.

It should be noted that the dimensions of the excimer lamp 20 is not limited to the above sizes when there is no particular need for downsizing. However, as there is a case in which breakdown does not occur within the arc tube 22 if the distance between the electrodes is large, it is preferable that the dimensions are set in relation to an applied voltage.

The casing 12 is in a U shape. The casing 12 includes a first protecting portion 14a provided so as to cover the first electrode 24 and a second protecting portion 14b provided so as to cover the second electrode 25. The casing 12 also includes a connecting portion 16 that connects the first protecting portion 14a with the second protecting portion 14b. In other words, the casing 12 is configured such that the first protecting portion 14a, the connecting portion 16, and the second protecting portion 14b are integrally formed into the casing 12 in the U shape. Further, the first protecting portion 14a and the second protecting portion 14b are apart from each other.

With the ozone generating device 10 the first electrode 24 is covered by the first protecting portion 14a, the second electrode 25 is covered by the second protecting portion 14b, and the first protecting portion 14a and the second protecting portion 14b are apart from each other. Therefore, the first electrode 24 and the second electrode 25 are covered by a protecting portion 14 (the first protecting portion 14a and the second protecting portion 14b), and a tube-axial direction central portion of the arc tube 22 is exposed. With such a configuration, without shielding light emitted from the arc tube 22 largely, it is possible to cover the electrodes (the first electrode 24 and the second electrode 25) by the protecting portion 14 (the first protecting portion 14a and the second protecting portion 14b). With this, it is possible to prevent the electrodes from being deteriorated by ozone while maintaining the ozone generation efficiency high. Further, it is possible to prevent moisture present in a use environment from reaching an electrode portion.

In the protecting portion 14 (the first protecting portion 14a and the second protecting portion 14b), an opening 18 corresponding to a tube diameter of the arc tube 22 is provided. As the protecting portion 14 is provided with the opening 18 corresponding to the tube diameter of the arc tube 22, the arc tube 22 may be provided in the opening 18. Further, as the opening 18 is an opening corresponding to the tube diameter of the arc tube 22, it is possible to prevent ozone generated outside the casing 12 from entering inside of the casing 12 as much as possible.

The arc tube 22 and the connecting portion 16 are apart from each other, and a ventilation region 32 is provided between the arc tube 22 and the connecting portion 16. As the arc tube 22 and the connecting portion 16 are apart from each other, and the ventilation region 32 is provided therebetween, light emitted from the arc tube 22 can be efficiently irradiated to oxygen from all direction of the arc tube 22, and thus it is possible to increase an amount of generated ozone. Further, as the arc tube 22 and the connecting portion 16 are apart from each other, it is possible to prevent the connecting portion 16 from being deteriorated by light emitted from the arc tube 22. In other words, as the light emitted from the arc tube 22 is irradiated to oxygen and weakened in the ventilation region 32, it is possible to prevent deterioration of the connecting portion 16.

In terms of preventing deterioration of the connecting portion 16 and increasing an amount of generated ozone, a separation distance between the arc tube 22 and the connecting portion 16 is preferably 1 mm or greater, more preferably 5 mm or greater, and further preferably 10 mm or greater. Further, in terms of downsizing of the ozone generating device 10, the separation distance is preferably 30 mm or smaller, more preferably 25 mm or smaller, and further preferably 20 mm or smaller. Here, the separation distance between the arc tube and the connecting portion means a distance between portions of the arc tube and the connecting portion that are closest to each other.

As shown in FIG. 2, the electronic component 36 such as an inverter for feeding power to the excimer lamp is contained within the casing 12. To the electronic component 36, the first electrode 24 and the second electrode 25 is directly connected, and the first electrode 24 and the second electrode 25 are fixed to the electronic component 36.

As the electronic component 36 is contained within the casing 12, it is possible to prevent the electronic component 36 from being influenced by external noise. Further, it is possible to prevent noises that can be produced by the electronic component 36 from leaking outside. Over an inner surface of the casing 12, a conventionally known electromagnetic shielding layer (e.g., a film for electromagnetic shielding) may be provided.

Hereinbefore, the ozone generating device 10 has been described.

In the embodiment described above, the case in which the first electrode 24 is not provided over the first diameter-reduced portion 33a and the second electrode 25 is not provided over the second diameter-reduced portion 33b has been described. Specifically, the case in which no electrode is provided for either of the first diameter-reduced portion and the second diameter-reduced portion has been described. However, the present invention is not limited to such an example, and it is possible to provide a configuration in which an electrode is provided over one of the first diameter-reduced portion and the second diameter-reduced portion and no electrode is provided over the other of the diameter-reduced portions. This is because with the diameter-reduced portion over which no electrode is provided, it is possible to reduce risks of breakage.

Here, one of the diameter-reduced portions that is closed last when the luminescent gas is enclosed into the arc tube is referred to as the second diameter-reduced portion. Due to manufacturing reasons, as compared to the first diameter-reduced portion, the thickness of the second diameter-reduced portion easily becomes uneven, and it is also difficult to decrease its diameter evenly. Accordingly, as compared to the first diameter-reduced portion, the second diameter-reduced portion is a portion that becomes easily broken. Therefore, when the configuration in which an electrode is provided over one of the first diameter-reduced portion and the second diameter-reduced portion, and no electrode is provided over the other of the diameter-reduced portions is employed, it is preferable to employ a configuration in which a second electrode is not provided over the second diameter-reduced portion.

Figure 5:
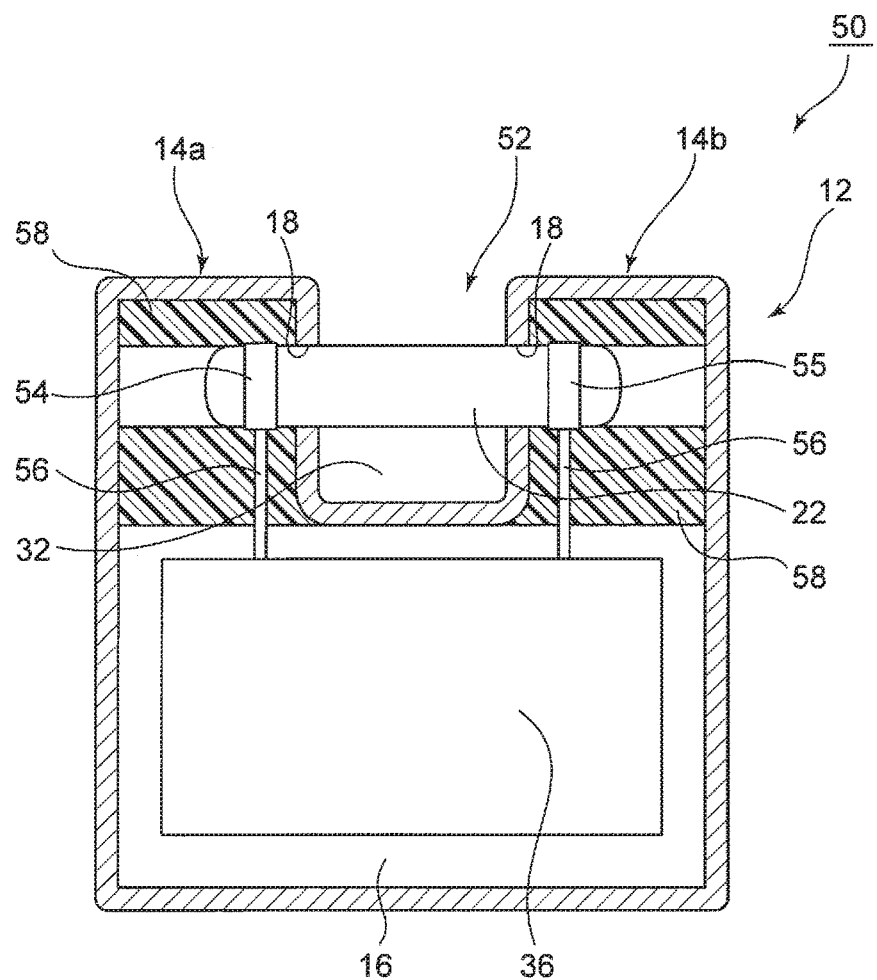
FIG. 5 is a front view of an ozone generating device according to a different embodiment, with a front half of its casing removed for illustration.

FIG. 5 is a front view of an ozone generating device according to a different embodiment, with a front half of its casing removed for illustration.

An ozone generating device 50 shown in FIG. 5 is different from the ozone generating device 10 in the configuration of the first electrode and the second electrode, the method for connecting the first electrode with the electronic component, and the method for connecting the second electrode with the electronic component, and in that a fixation member 58 is provided, but is otherwise identical. Therefore, in the following description, the differences are mainly described and descriptions of the identical portions shall be omitted. It should be noted that like components as those of the ozone generating device 10 are represented by like reference numerals.

The ozone generating device 50 shown in FIG. 5 includes the casing 12 and an excimer lamp 52. As the casing 12 has been already described, a description thereof shall be omitted.

The excimer lamp 52 includes the arc tube 22 in which a luminescent gas is contained, a first electrode 54, and a second electrode 55. As the arc tube 22 has been already described, a description thereof shall be omitted.

The first electrode 54 is provided over the outer periphery surface of the first end portion 31a. The second electrode 55 is provided over the outer periphery surface of the second end portion 31b. It should be noted that the first electrode 54 and the second electrode 55 are not provided with an extending portion like the first electrode 24 and the second electrode 25.

While shapes of the first electrode 54 and the second electrode 55 are not particularly limited, a cylindrical shape as in this embodiment is preferable. This is because it is possible to perform dielectric-barrier discharge more advantageously if the shape is cylindrical. Different examples of the shape of the first electrode 54 and the second electrode 55 include a shape having a C-shaped cross section and a coiled shape.

A material of the first electrode 54 and the second electrode 55 is not particularly limited, but stainless steel and kanthal (iron-chromium alloy) are preferable in terms of an oxidation resistance and a thermal shock resistance at high temperatures.

The first electrode 54 and the electronic component 36 are electrically connected with each other by a wiring 56. Further, the second electrode 55 and the electronic component 36 are electrically connected with each other by the wiring 56.

Within the protecting portion 14 (the first protecting portion 14a and the second protecting portion 14b), the fixation member 58 is filled in a state in which the fixation member is not in contact with the first diameter-reduced portion 33a and the second diameter-reduced portion 33b. With this, the arc tube 22 is fixed to the casing 12 via the electrodes (the first electrode 24 and the second electrode 25) and the fixation member 58. At this time, as the fixation member 58 is not in contact with the first diameter-reduced portion 33a and the second diameter-reduced portion 33b at which stresses are easily concentrated, it is possible to reduce risks of breakage.

The fixation member 58 is not particularly limited as long as the member is able to fix the electrodes (the first electrode and the second electrode) to any member that constitutes the ozone generating device, but examples include an inorganic adhesive and a silicon resin that are conventionally known.

Hereinbefore, the ozone generating device 50 has been described.

In the embodiment described above, the case in which the fixation member 58 is only filled within the protecting portion 14 has been described, but the fixation member 58 may be filled within a portion other than the protecting portion 14 (e.g., the connecting portion 16).

In the embodiment described above, the configuration in which the fixation member 58 is not provided at a position to which the diameter-reduced portions of the arc tube 22 (the first diameter-reduced portion 33a and the second diameter-reduced portion 33b) face, and light from diameter-reduced portion directly reach an inner wall of the protecting portion has been described. However, the present invention is not limited to such an example, and the fixation member may be filled between the diameter-reduced portion and the inner wall of the protecting portion in a state in which the fixation member is not in contact with the diameter-reduced portion. In this case, it is possible to reduce light emitted from the diameter-reduced portion of the arc tube from reaching the inner wall of the protecting portion, and it is possible to prevent deterioration of the inner wall due to the light.

In the embodiment described above, the configuration in which the fixation member 58 is filled within the protecting portion 14 so as to be in contact not only with the electrodes (the first electrode 54 and the second electrode 55) but also with the arc tube 22 has been described. However, the present invention is not limited to such an example, and the fixation member may be filled within the protecting portion so as to be in contact only with the electrodes and not with the arc tube.

Further, the fixation member may be filled within the protecting portion so as to be in contact with one of the first electrode and the second electrode, and not with the other of the electrodes. This is because the arc tube may be fixed to the ozone generating device when at least one of the electrodes is fixed via the fixation member.

As described above, the fixation of the arc tube according to the present invention may be such that the arc tube is fixed directly via the electrodes (the first electrode and the second electrode) like the ozone generating device 10, or the arc tube is fixed further via another member (e.g., a fixation member 56) in addition to the electrodes like the ozone generating device 50.

In the embodiment described above, the case in which the cylindrical portion of the arc tube is fixed via the first electrode and the second electrode has been described. However, in the present invention is not limited to such an example in which the fixation is carried out via the first electrode and the second electrode, as long as the arc tube is fixed at the cylindrical portion. Hereinafter, a case in which the cylindrical portion of the arc tube is fixed without via the first electrode and the second electrode will be described with reference to FIG. 6 and FIG. 7.

Figure 6:
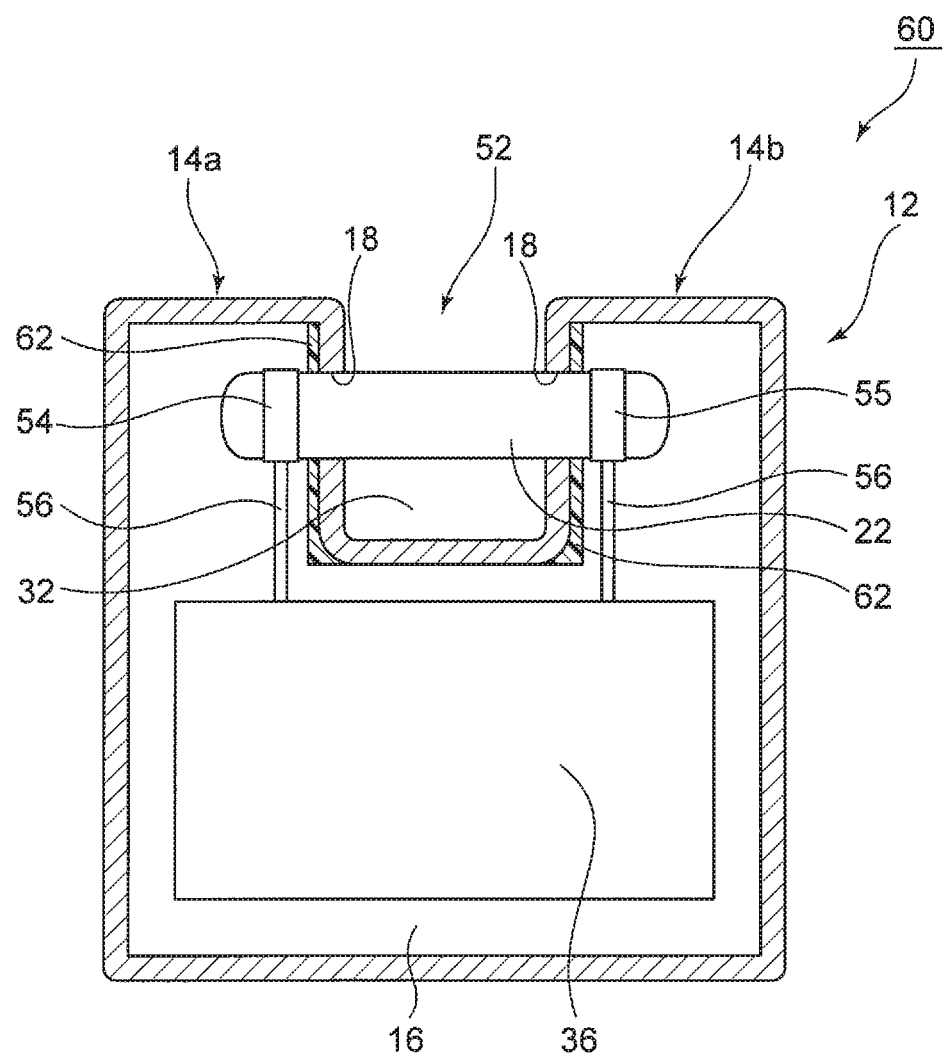
FIG. 6 is a schematic view for illustration of an ozone generating device according to a different embodiment.

FIG. 6 is a schematic view for illustration of an ozone generating device according to a different embodiment.

An ozone generating device 60 shown in FIG. 6 is such that a fixation member 62 is filled within the protecting portion 14 (the first protecting portion 14a and the second protecting portion 14b) in a state in which the fixation member is not in contact with the electrodes (the first electrode 54 and the second electrode 55). In other words, in the ozone generating device 60, the cylindrical portion 30 of an arc tube 52 is fixed to the casing 12 via the fixation member 62. Here, the ozone generating device 60 is the same as the ozone generating device 50 other than this point, and not described here. It should be noted that like components as those of the ozone generating device 50 are represented by like reference numerals.

Figure 7:
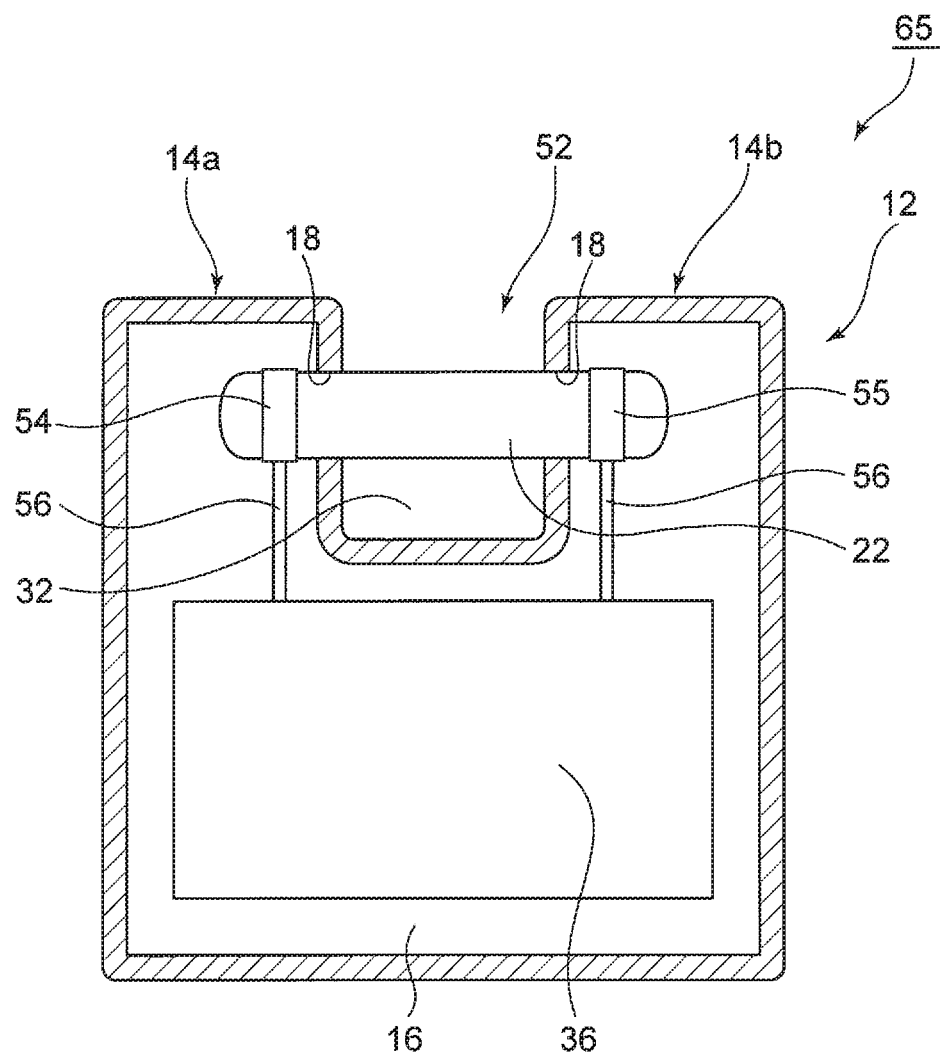
FIG. 7 is a schematic view for illustration of an ozone generating device according to a different embodiment.

FIG. 7 is a schematic view for illustration of an ozone generating device according to a different embodiment.

An ozone generating device 65 shown in FIG. 7 is such that the fixation member is not filled within the protecting portion 14 (the first protecting portion 14a and the second protecting portion 14b). In other words, is such that the ozone generating device 65, the cylindrical portion 30 of the arc tube 52 is fixed to the casing 12 via the opening 18. Here, the ozone generating device 65 is the same as the ozone generating device 50 other than this point, and not described here. It should be noted that like components as those of the ozone generating device 50 are represented by like reference numerals.

In the embodiment described above, the case in which the ozone generating device is provided with a casing has been described. However, according to the present invention, the ozone generating device may not be provided with a casing. Hereinafter, this case will be described with reference to FIG. 8.

Figure 8:
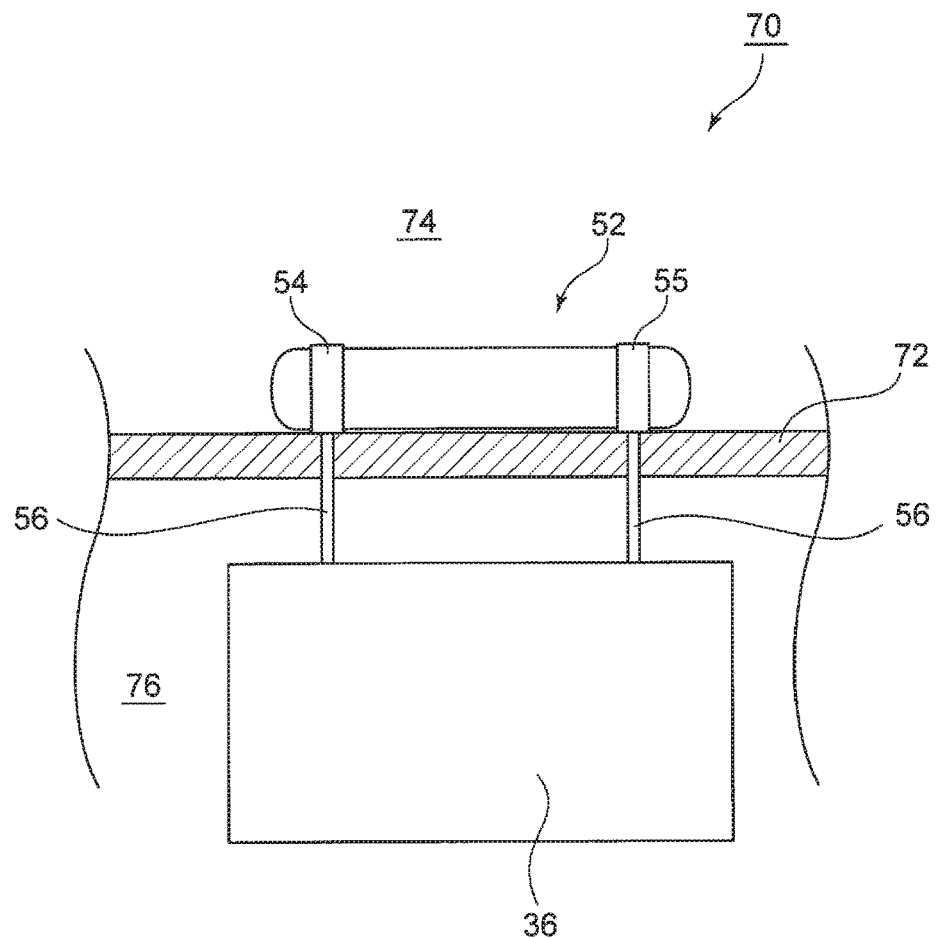
FIG. 8 is a schematic view for illustration of an ozone generating device according to a different embodiment.

FIG. 8 is a schematic view for illustration of an ozone generating device according to a different embodiment.

An ozone generating device 70 shown in FIG. 8 is different from the ozone generating device 50 in that a casing is not provided, but is otherwise identical. Therefore, in the following description, the difference is mainly described and descriptions of the identical portions shall be omitted. It should be noted that like components as those of the ozone generating device 50 are represented by like reference numerals.

The ozone generating device 70 shown in FIG. 8 includes the excimer lamp 52. As the excimer lamp 52 has been already described, a description thereof shall be omitted.

The excimer lamp 52 is fixed to an installation object 72 so that the arc tube 22 is exposed to a space 74 in which ozone is to be generated. The method of fixation of the excimer lamp to the installation object 72 is not particularly limited, but examples include a method of fixing the electrodes (the first electrode 54 and the second electrode 55) to the installation object 72 by an adhesive or the like. In a space 76 that is on an opposite side of the space 74 of the installation object 72, the electronic component 36 is placed. The first electrode 54 and the electronic component 36 are electrically connected to each other by the wiring 56 inserted through a through hole provided in the installation object 72. Further, the second electrode 55 and the electronic component 36 are electrically connected to each other by the wiring 56 inserted through the through hole provided in the installation object 72. In this manner, the ozone generating device may be configured to include the excimer lamp and the electronic component without a casing.

It should be noted that examples of the installation object 72 include a wall surface of an air conditioning duct 82 of an in-car the air conditioning device 80 that will be later described. In this case, the excimer lamp 52 may be placed within the air conditioning duct 82, and the electronic component 36 may be placed outside the air conditioning duct 82, for example.

Next, an in-car air conditioning device having an ozone generating device will be described.

Figure 9:
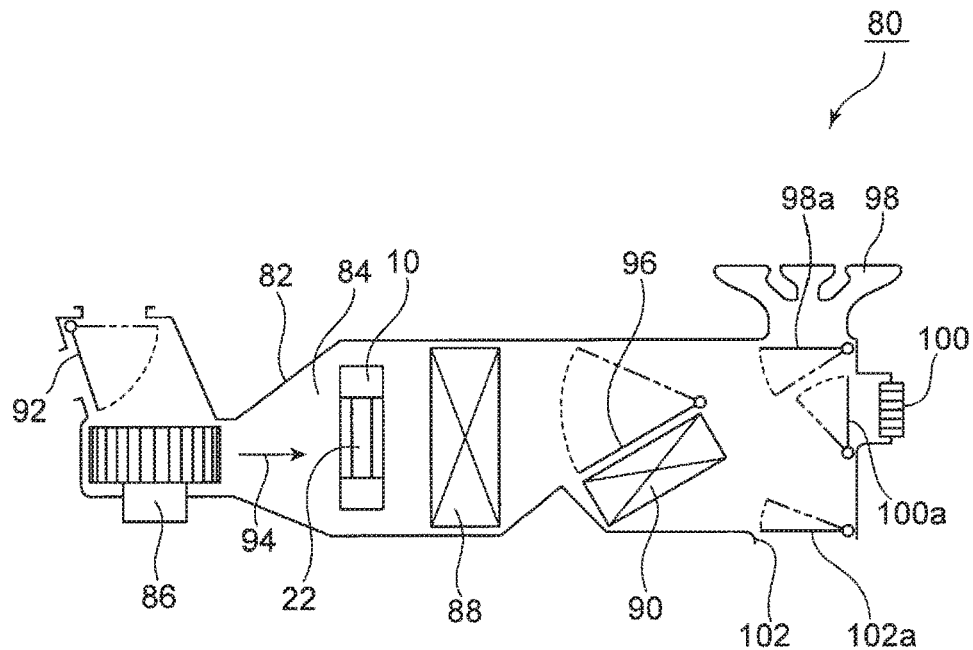
FIG. 9 is a conceptual diagram of an in-car air conditioning device according to a first embodiment.

FIG. 9 is a conceptual diagram of an in-car air conditioning device according to this embodiment. As shown in FIG. 9, the in-car air conditioning device 80 includes the air conditioning duct 82, and a flow channel 84 is formed within the air conditioning duct 82.

At an inlet of the air conditioning duct 82, an intake door 92 is provided for switching between an external air intake mode and an internal air circulation mode.

On a downstream side of the intake door 92, an air blower 86 for intake of air from outside of the vehicle is provided. By the air blower 86, it is possible to send air in a direction of an arrow 94.

On downstream of the air blower 86, an evaporating device (evaporator) 88 for cooling air from the air blower 86 is provided.

On downstream of the evaporating device 88, an air-mix door 96 is provided. The air-mix door 96 is a switching device that to allow air that passes the evaporating device 88 directly into a cabin or to allow air that after passing through a heater 90 into a cabin.

On downstream of the air-mix door 96, the heater 90 for heating air that passes the evaporating device 88 is provided.

Between the air blower 86 and the evaporating device 88 (on an upstream side of the evaporating device 88), the ozone generating device 10 is provided. The ozone generating device 10 is provided such that a tube-axial direction of the arc tube 22 and an air-blowing direction intersect each other. As the ozone generating device 10 is provided such that the tube-axial direction of the arc tube 22 and the air-blowing direction intersect each other, it is possible to efficiently treat a larger amount of oxygen by light emitted from the arc tube 22.

Regarding an outlet side of the air conditioning duct 82 (rightward in FIG. 9), a defroster nozzle 98 is provided on an upper side, a bent outlet nozzle 100 is provided on a middle side, and a heater outlet nozzle 102 is provided on a lower side (below leg). The nozzles 98, 100, and 102 are respectively provided with mode doors 98a, 100a, and 102a that can be opened and closed.

According to the ozone generating device 10, as risks of breakage of the arc tube 22 due to oscillation and the like is reduced, risks of breakage of the arc tube due to oscillation and the like of the in-car air conditioning device 80 having the ozone generating device 10 is also reduced. As a result, the in-car air conditioning device 80 may be advantageously mounted on a vehicle on which oscillation and the like can frequently occur. Further, according to the in-car air conditioning device 80, bacteria and the like generated over a surface of the evaporating device 88 may be sterilized by ozone generated by the ozone generating device 10. With this, it is possible to suppress an offensive smell and the like due to bacteria and the like.

In the embodiment described above, the case in which within the flow channel 84 of the in-car air conditioning device 80, the air blower 86, the evaporating device 88, the heater 90, and the ozone generating device 10 are disposed in an order from the upstream side has been described. However, the present invention is not limited to the example order stated above, as long as bacteria generated over the surface of the evaporating device may be sterilized by ozone generated by the ozone generating device. As it is possible to sterilize bacteria attached to the evaporating device and substances of offensive smell efficiently by ozone, it is preferable that the ozone generating device is disposed on the upstream side of the evaporating device.

In the embodiment described above, the case in which the air conditioning device of the present invention is for an in-car use has been described, but applications of the air conditioning device of the present invention are not limited to the in-car use. As risks of breakage of the arc tube due to oscillation and the like is reduced, the ozone generating device may be advantageously used for air conditioning devices in any application having a member such as an air blower with which oscillation and the like can occur.

Next, a vehicle having an air conditioning device will be described.

The vehicle according to this embodiment includes an air conditioning device 80. The air conditioning device 80 is such that the ozone generating device 10 is positioned so that a direction perpendicular to a floor surface of the vehicle matches the tube-axial direction of the arc tube 22. As the positioning is such that the direction perpendicular to the floor surface of the vehicle matches the tube-axial direction of the arc tube 22, it is possible to suppress breakage of the arc tube due to up-down vibration (vertical vibration) when the vehicle travels. However, the vehicle of the present invention is not particularly limited, as long as the air conditioning device having the ozone generating device is provided.

As the ozone generating device 10 can be easily made small, the air conditioning device 80 having the ozone generating device 10 can also be made small. As a result, the air conditioning device 80 is advantageously mounted on a vehicle with a limited space.

Hereinbefore, the first embodiment has been described.

Second Embodiment

Figure 10:
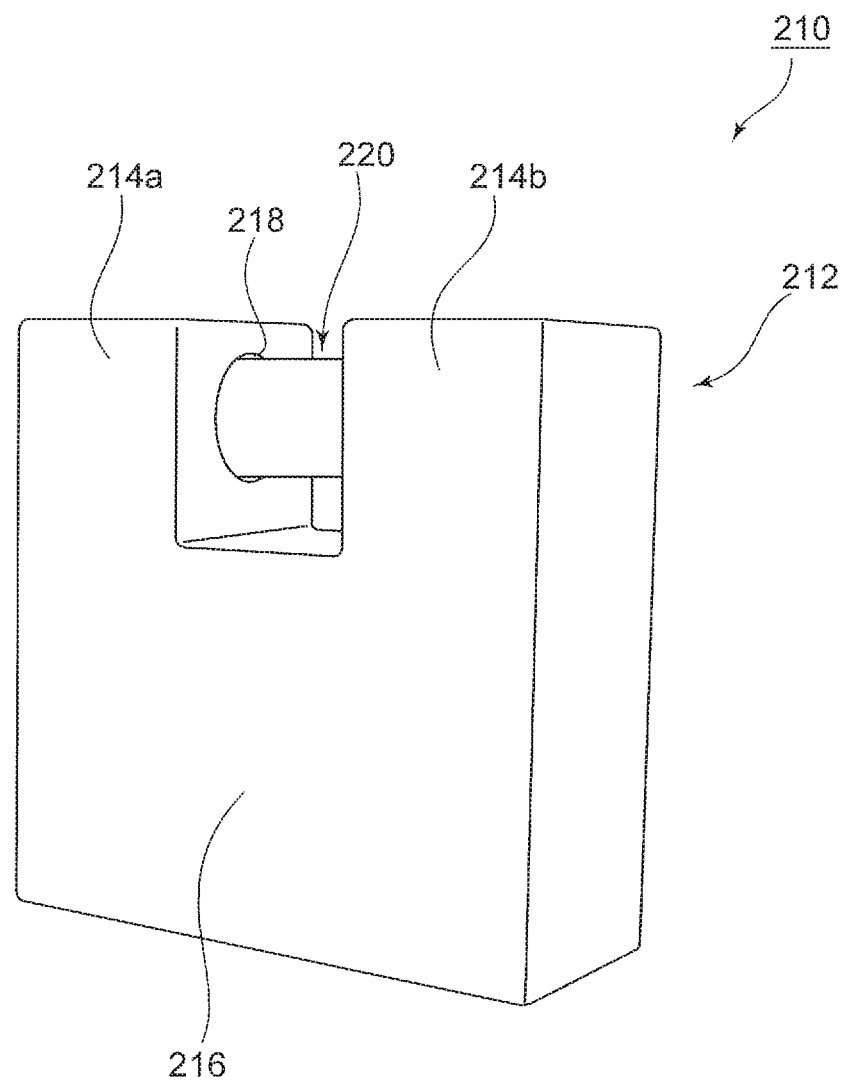
FIG. 10 is a perspective view schematically showing an ozone generating device according to a second embodiment.
Figure 11:
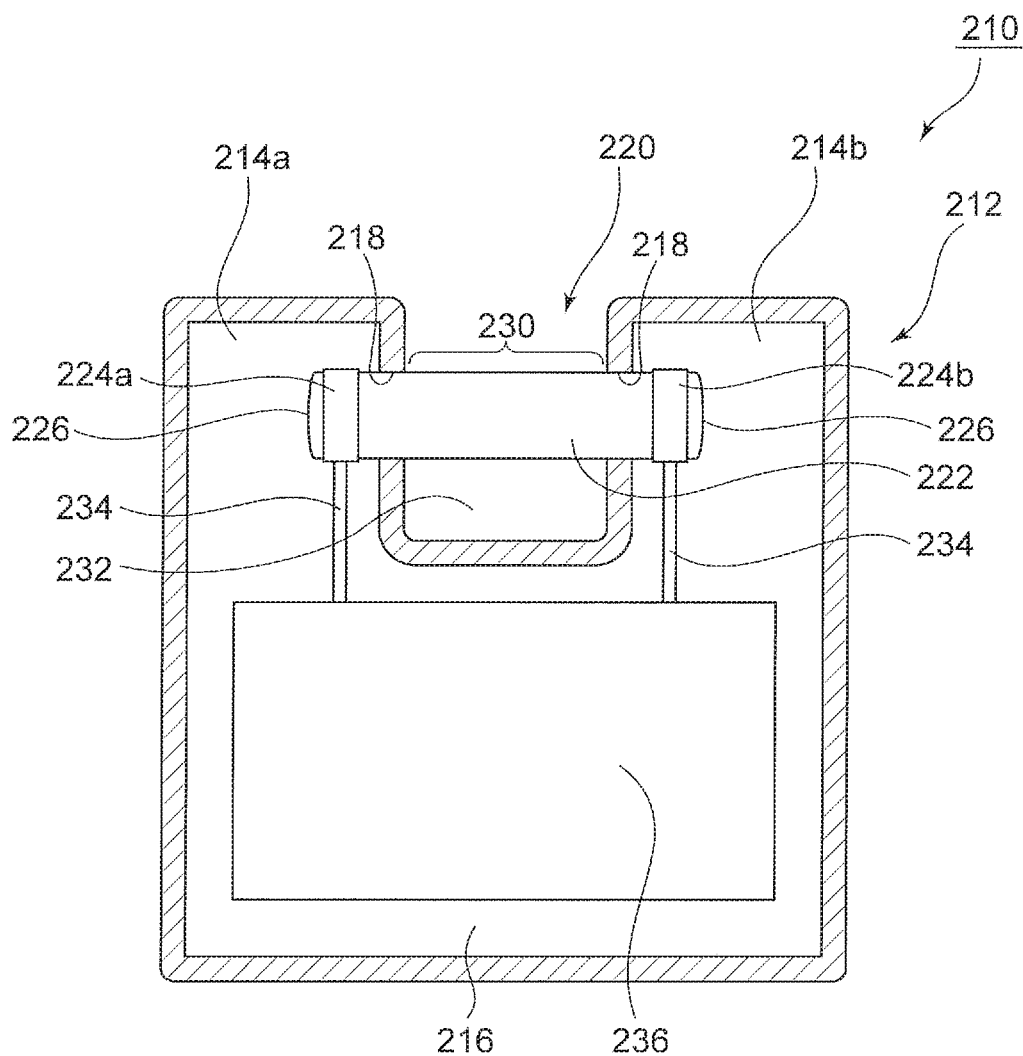
FIG. 11 is a front view of the ozone generating device shown in FIG. 10, with a front half of its casing removed for illustration.

FIG. 10 is a perspective view schematically showing an ozone generating device according to a second embodiment. FIG. 11 is a front view of the ozone generating device shown in FIG. 10, with a front half of its casing removed for illustration.

As shown in FIG. 10 and FIG. 11, an ozone generating device 210 includes a casing 212 and an excimer lamp 220.

Figure 12:
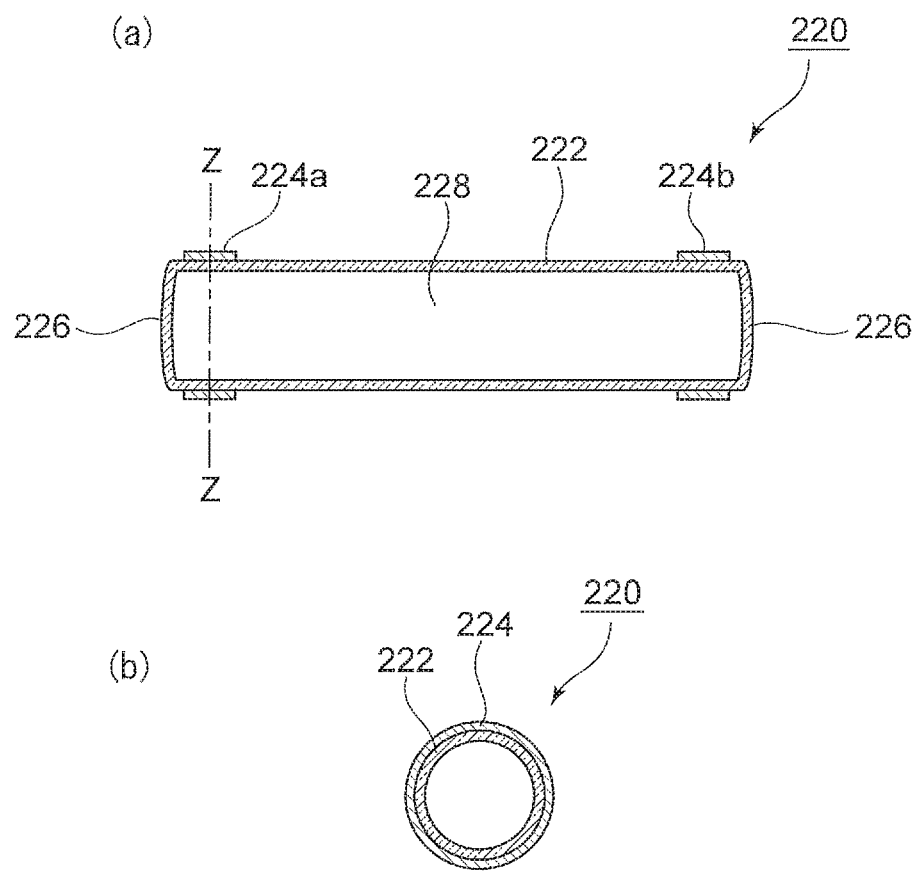
FIG. 12(a) is a sectional view of an excimer lamp provided for the ozone generating device shown in FIG. 10 in a tube-axial direction.
FIG. 12(b) is a sectional view of this excimer lamp taken along line Z-Z.

FIG. 12 (a) is a sectional view of an excimer lamp provided for the ozone generating device shown in FIG. 10 in a tube-axial direction, and FIG. 12 (b) is a sectional view of this excimer lamp taken along line Z-Z.

The excimer lamp 220 includes an arc tube 222 in which a luminescent gas is contained, and electrodes 224 (an electrode 224a, an electrode 224b) provided for an outer periphery surface at both end portions of the arc tube 222 in the tube-axial direction.

It should be noted that while this embodiment describes a case in which the excimer lamp 220 is an excimer lamp utilizing dielectric-barrier discharge, the excimer lamp of the present invention may be any excimer that emits light from excimer, and the present invention is not limited to the case in which dielectric-barrier discharge is utilized.

While a shape of the arc tube 222 is not particularly limited as long as the shape is tubular with a sealed interior, a circular tube shape with both ends sealed is preferable as in this embodiment.

While a material of the arc tube 222 is not particularly limited, it is preferable to use a material that passes ultraviolet light, such as quartz glass, for example.

A type of the luminescent gas is not particularly limited, as long as the gas is able to emit light of wavelength that allows generation of ozone when irradiated to oxygen. Examples of the luminescent gas include xenon (output wavelength: 172 nm), krypton chloride (output wavelength: 222 nm), and krypton bromide (output wavelength: 207 nm).

As described above, the electrodes 224 are provided for the outer periphery surface at the both end portions of the arc tube 222 in the tube-axial direction. It is preferable that the electrodes 224 are provided at cylindrical portions of the outer periphery surface of the arc tube 222, and the shape is not particularly limited but a cylindrical shape is preferable as in this embodiment. This is because it is possible to perform dielectric-barrier discharge more advantageously if the shape is cylindrical. Different examples of the shape of the electrode include a shape having a C-shaped cross section and a coiled shape.

It is more preferable that an area that the electrodes 224 cover the outer periphery surface of the arc tube 222 is larger, in terms of startability. Therefore, it is preferable that the shape is cylindrical as in this embodiment.

It should be noted that it is preferable that the electrodes 224 are not provided at end surfaces 226 of the arc tube 222. This is because the end portions of the arc tube include portions with low strength.

While a material of the electrodes 224 is not particularly limited, but stainless steel and kanthal (iron-chromium alloy) are preferable in terms of an oxidation resistance and a thermal shock resistance at high temperatures.

According to the excimer lamp 220, when an alternating-current high voltage is applied between the electrodes 224, dielectric-barrier discharge is induced in a space 228 within the arc tube 222. Then, this excites the luminescent gas to be in an excimer state, and when the gas resumes an original state (ground state) from the excimer state, a spectrum unique to excimer is emitted (excimer emission).

With the excimer lamp 220, an electrode is not provided within its arc tube, but only on the outer periphery surface. Therefore, the excimer lamp 220 may be easily manufactured only by enclosing the luminescent gas within the arc tube 22 and then providing the electrodes 224 on the outer periphery surface.

Further, with the excimer lamp 220, an electrode is not provided within the arc tube, and wiring electrically connecting an interior with an exterior of the arc tube is not necessary. Therefore, there is no member that penetrate a wall surface of the arc tube 222. Accordingly, it is possible to maintain high reliability of the excimer lamp 220.

As described above, with the excimer lamp 220, electrodes are not provided within its arc tube, but only on the outer periphery surface. Therefore, it is possible to manufacture the excimer lamp 220 in small sizes. Because the excimer lamp 220 can be made easily in small sizes, dimensions of the excimer lamp 220 are as follows. An entire length in a tube-axial direction is preferably from 10 mm to 150 mm, more preferably from 10 mm to 100 mm, and further preferably from 10 mm to 50 mm. Further, a distance between the electrodes is preferably from 3 mm to 130 mm, more preferably from 3 mm to 80 mm, and further preferably from 3 mm to 30 mm. Here, the distance between the electrodes means a distance between portions of the electrodes that are closest to each other. Moreover, when the shape is cylindrical, an outer diameter is preferably from 3 mm to 20 mm, more preferably from 3 mm to 15 mm, and further preferably from 3 mm to 10 mm. Furthermore, a wall thickness of the arc tube 222 is preferably from 0.1 mm to 2 mm, more preferably from 0.1 mm to 1 mm, and further preferably from 0.1 mm to 0.5 mm.

It should be noted that the dimensions of the excimer lamp 220 is not limited to the above sizes when there is no particular need for downsizing. However, as there is a case in which breakdown does not occur within the arc tube 222 if the distance between the electrodes is large, it is preferable that the dimensions are set in relation to an applied voltage.

The casing 212 is in a U shape. The casing 212 includes a first protecting portion 214a provided so as to cover one of the electrodes 224 (the electrode 224a), and a second protecting portion 214b provided so as to cover the other of the electrodes 224 (the electrode 224b). The casing 212 also includes a connecting portion 216 that connects the first protecting portion 214a with the second protecting portion 214b. In other words, the casing 212 is configured such that the first protecting portion 214a, the connecting portion 216, and the second protecting portion 214b are integrally formed into the casing 212 in the U shape.

According to the ozone generating device 210, as the excimer lamp 220, an excimer lamp having the electrodes 224 provided for the outer periphery surface at the both end portions of the arc tube 222 in the tube-axial direction. Then, the electrodes 224 are covered by the protecting portions 214 (the first protecting portion 214a and the second protecting portion 214b). As a result, portions covered by the protecting portions 214 are the both end portions of the arc tube 222 in the tube-axial direction, and a tube-axial direction central portion 230 of the arc tube 222 is exposed. With such a configuration, without shielding light emitted from the arc tube 222 largely, it is possible to cover the electrodes 224 by the protecting portions 214. With this, it is possible to prevent the electrodes 224 from being deteriorated by ozone while maintaining the ozone generation efficiency high. Further, it is possible to prevent moisture present in a use environment from reaching an electrode portion.

Further, with the ozone generating device 210, the first protecting portion 214a, the connecting portion 216, and the second protecting portion 214b are integrally formed into the casing 212. Therefore, it is possible to hold the excimer lamp 220 stably by the first protecting portion 214a and the second protecting portion 214b.

In the protecting portion 214 (the first protecting portion 214a and the second protecting portion 214b), an opening 218 corresponding to a tube diameter of the arc tube 222 is provided. As the protecting portion 214 is provided with the opening 218 corresponding to the tube diameter of the arc tube 222, the excimer lamp 220 may be held by providing the arc tube 222 in the opening 218. Further, as the opening 218 is an opening corresponding to the tube diameter of the arc tube 222, it is possible to prevent ozone generated outside the casing 212 from entering the casing 212 as much as possible.

The arc tube 222 and the connecting portion 216 are apart from each other, and a ventilation region 232 is provided between the arc tube 222 and the connecting portion 216. As the arc tube 222 and the connecting portion 216 are apart from each other, and the ventilation region 232 is provided therebetween, light emitted from the arc tube 222 can be efficiently irradiated to oxygen from all direction of the arc tube 222, and thus it is possible to increase an amount of generated ozone. Further, as the arc tube 222 and the connecting portion 216 are apart from each other, it is possible to prevent the connecting portion 216 from being deteriorated by light emitted from the arc tube 222. In other words, as the light emitted from the arc tube 222 is irradiated to oxygen and weakened in the ventilation region 232, it is possible to prevent deterioration of the connecting portion 216.

In terms of preventing deterioration of the connecting portion 216 and increasing an amount of generated ozone, a separation distance between the arc tube 222 and the connecting portion 216 is preferably 1 mm or greater, more preferably 5 mm or greater, and further preferably 10 mm or greater. Further, in terms of downsizing of the ozone generating device 210, the separation distance is preferably 30 mm or smaller, more preferably 25 mm or smaller, and further preferably 20 mm or smaller. Here, the separation distance between the arc tube and the connecting portion means a distance between portions of the arc tube and the connecting portion that are closest to each other.

As shown in FIG. 11, the electronic component 236 such as an inverter for feeding power to the excimer lamp is contained within the casing 212. The electronic component 236 and the electrodes 224 of the excimer lamp 220 are electrically connected by wiring 234. As the electronic component 236 is contained within the casing 212, it is possible to prevent the electronic component 236 from being influenced by external noise. Further, it is possible to prevent noises that can be produced by the electronic component 236 from leaking outside. Over an inner surface of the casing 212, a conventionally known electromagnetic shielding layer (e.g., a film for electromagnetic shielding) may be provided.

Hereinbefore, the ozone generating device 210 has been described.

Figure 13:
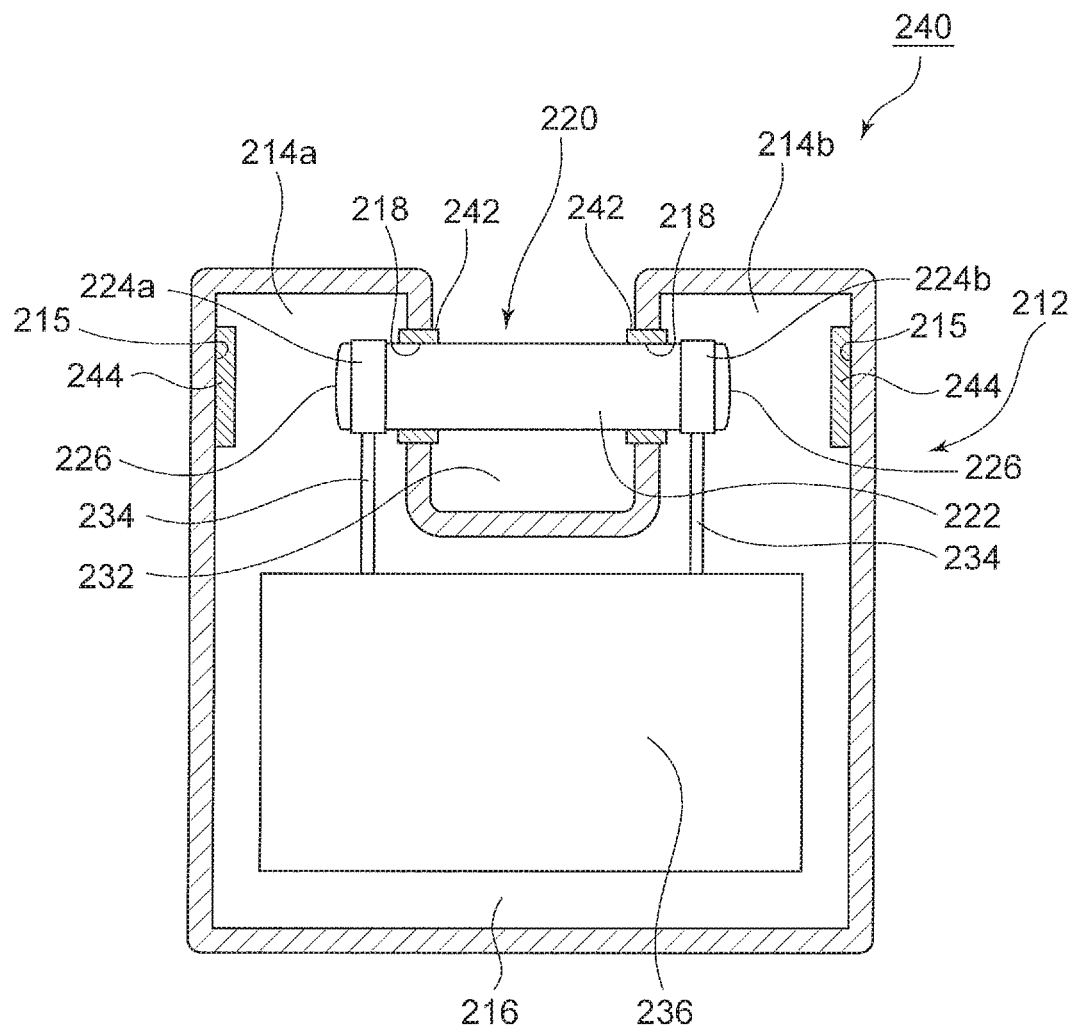
FIG. 13 is a front view of an ozone generating device according to a different embodiment, with a front half of its casing removed for illustration.

FIG. 13 is a front view of an ozone generating device according to a different embodiment, with a front half of its casing removed for illustration.

An ozone generating device 240 shown in FIG. 13 is different from the ozone generating device 210 that a first light shielding member 242 is provided and a second light shielding member 244 is provided, but is otherwise identical. Therefore, in the following description, the difference is mainly described and descriptions of the identical portions shall be omitted. It should be noted that like components as those of the ozone generating device 210 are represented by like reference numerals.

The ozone generating device 240 shown in FIG. 13 is provided with the first light shielding member 242 for shielding light emitted from the arc tube 222, between the opening 218 and the arc tube 222. As the first light shielding member 242 is provided, light emitted from the arc tube 222 is prevented from reaching the opening 218 of the protecting portions 214, and it is possible to suppress deterioration of a portion of the opening 218 due to the light.

While a material of the first light shielding member 242 is not particularly limited, it is preferable to use a material that is less susceptible to deterioration due to light emitted from the arc tube 222 (e.g., ultraviolet light), such as fluorine resin.

While a shape of the first light shielding member 242 is not particularly limited, a cylindrical shape is preferable. This is because if the first light shielding member 242 is in a cylindrical shape, it is possible to cover the opening 218 entirely.

Further, the ozone generating device 240 is provided with the second light shielding member 244 at an inner wall 215 of the protecting portions 214 that face against the end surface 226 of the arc tube 222 and the end surface 226 of the arc tube 222. As the second light shielding member 244 is provided, light emitted from the end surface 226 of the arc tube 222 is prevented from reaching the inner wall 215, and it is possible to suppress deterioration of the inner wall 215 (the protecting portions 214) by the light.

While a material of the second light shielding member 244 is not particularly limited, it is possible to use the same material as the first light shielding member 242.

It should be noted that in the embodiment described above, the case in which the second light shielding member 244 is provided for the inner wall 215 of the protecting portions 214 has been described, but the position of the second light shielding member according to the present invention is not limited to this example, and may be between the end surface of the arc tube and the inner wall of the protecting portion. For example, it is possible to provide for the end surface of the arc tube, or to provide such that a space between the end surface of the arc tube and the inner wall of the protecting portion is filled with a second light shielding member.

Hereinbefore, the ozone generating device 240 has been described.

Figure 14:
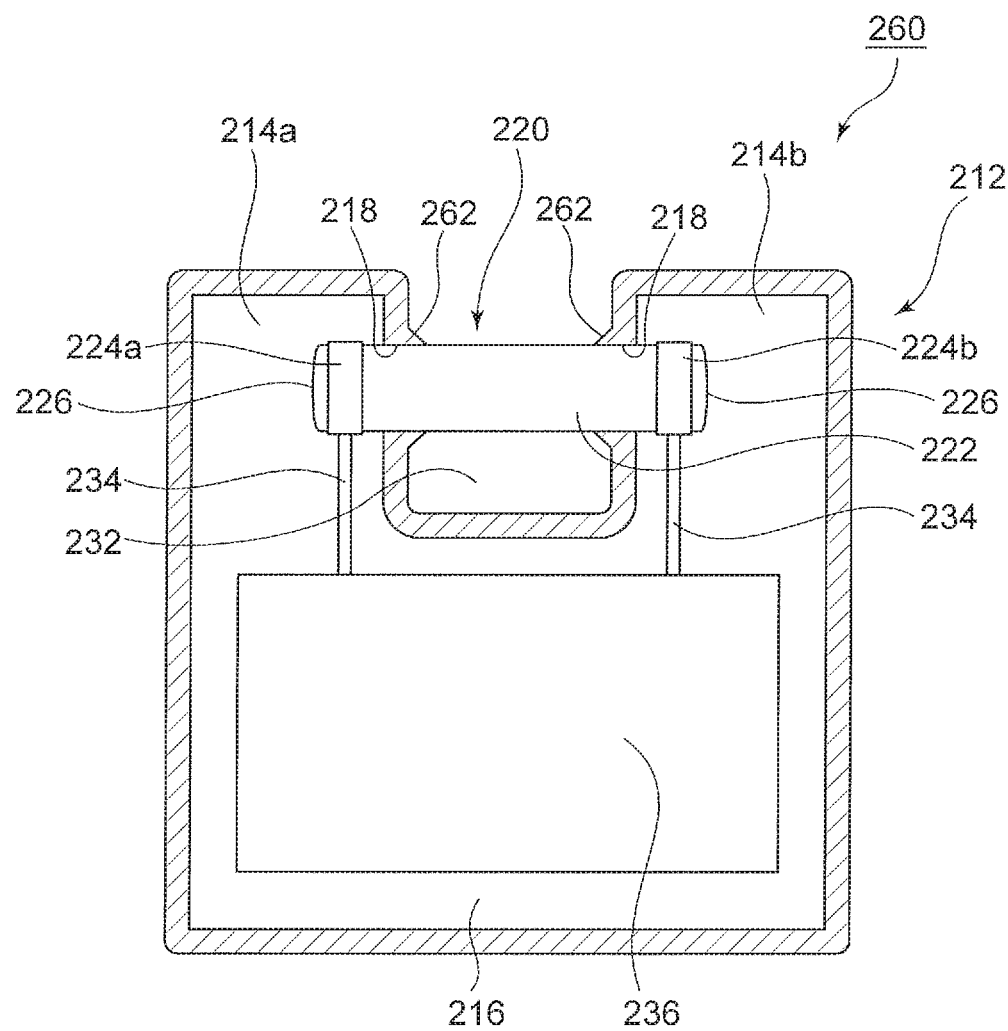
FIG. 14 is a front view of an ozone generating device according to a different embodiment, with a front half of its casing removed for illustration.

FIG. 14 is a front view of an ozone generating device according to a different embodiment, with a front half of its casing removed for illustration.

An ozone generating device 260 shown in FIG. 14 is different from the ozone generating device 210 in that a tapered portion is provided around an opening of a protecting portion, but is otherwise identical. Therefore, in the following description, the difference is mainly described and descriptions of the identical portions shall be omitted. It should be noted that like components as those of the ozone generating device 210 are represented by like reference numerals.

The ozone generating device 260 shown in FIG. 14 is provided with a tapered portion 262 around the opening 218 of the protecting portions 214. The tapered portion 262 may be provided integrally along with the protecting portions 214, or provided for the protecting portions 214 separately. As the tapered portion 262 is provided around the opening 218 of the protecting portions 214, ozone may not easily reach the protecting portions 214. Further, the arc tube 222 may be held by a surface around the opening 218 including the tapered portion 262, and breakage may be reduced.

Hereinbefore, the ozone generating device 260 has been described.

In the embodiment described above, the case in which the protecting portion is a part of the casing has been described. In other words, the case in which the electrode is covered by the protecting portion as a part of the casing has been described. However, the protecting portion of the present invention is not limited to the casing. For example, the protecting portion may be provided by applying an adhesive to the electrode and hardening the adhesive. In other words, the protecting portion may be an adhesive after hardening provided so as to cover the electrode.

Next, an in-car air conditioning device having an ozone generating device will be described.

Examples of the in-car air conditioning device according to the second embodiment include an in-car air conditioning device that is similar to the in-car air conditioning device 80 (cf. FIG. 9) described according to the first embodiment. In other words, the examples include the in-car air conditioning device 80 described according to the first embodiment having the ozone generating device 210 described according to the second embodiment, in place of the ozone generating device 10. As the in-car air conditioning device has been described according to the first embodiment, a description shall be omitted here.

Next, a vehicle having an air conditioning device will be described.

Examples of the vehicle according to the second embodiment include a vehicle that is similar to the vehicle described according to the first embodiment. In other words, the examples include the vehicle described according to the first embodiment having the ozone generating device 210 described according to the second embodiment, in place of the ozone generating device 10. As the vehicle has been described according to the first embodiment, a description shall be omitted here.

Hereinbefore, the embodiments according to the present invention (the first invention and the second invention) has been described. However, the present invention (the first invention and the second invention) is not limited to the above examples, and appropriate modification can be made within the scope that satisfy the configurations of the present invention (the first invention and the second invention).

DESCRIPTION OF REFERENCE SIGNS

10, 50, 60, 65, 70 ozone generating device
12 casing
14 protecting portion (the first protecting portion 14*a* and the second protecting portion 14*b*)
16 connecting portion
18 opening
20 excimer lamp
22 arc tube
24 first electrode
25 second electrode
28 space
30 cylindrical portion
31*a* first end portion
31*b* second end portion
33*a* first diameter-reduced portion
33*b* second diameter-reduced portion
34*a*, 34*b* end surface
32 ventilation region
36 electronic component
41 electrode main body
42 extending portion
43 electrode main body
44 extending portion
72 installation object
74 space
80 in-car air conditioning device
84 flow channel
86 air blower
88 evaporating device
90 heater
210, 240, 260 ozone generating device
212 casing
214 protecting portion (first protecting portion 214*a* and second protecting portion 214*b*)
215 inner wall
216 connecting portion
218 opening
220 excimer lamp
222 arc tube
224 electrode (electrode 224*a* and electrode 224*b*)
226 end surface
228 space
230 central portion
232 ventilation region
234 wiring
236 electronic component
242 first light shielding member
244 second light shielding member
262 tapered portion

The invention claimed is:

1. An ozone generating device, comprising:
an excimer lamp having an arc tube in which a luminescent gas is enclosed, a first electrode, a second electrode, and a casing, wherein
a main emission wavelength of the excimer lamp is 200 nm or lower,
the arc tube includes a cylindrical portion having a first end portion and a second end portion, a first diameter-reduced portion provided continuously from the first end portion, a diameter of which decreases as a distance from the first end portion increases, and a second diameter-reduced portion provided continuously from the second end portion, a diameter of which decreases as a distance from the second end portion increases,
the first electrode is provided for an outer periphery surface of the first end portion,
the second electrode is provided for an outer periphery surface of the second end portion,
the cylindrical portion of the arc tube is fixed to the casing via the first electrode and the second electrode, via a fixation member contained within the casing, or in direct contact with the casing, the first electrode is not provided over the first diameter-reduced portion, and/or the second electrode is not provided over the second diameter-reduced portion, and an entirety of a tube-axial direction central portion of the cylindrical portion is exposed apart from the casing.

2. The ozone generating device according to claim 1, wherein the first electrode is not provided over the first diameter-reduced portion, and the second electrode is not provided over the second diameter-reduced portion.

3. The ozone generating device according to claim 1, further comprising:

a first protecting portion provided so as to cover the first electrode; and a second protecting portion provided so as to cover the second electrode, wherein the first protecting portion and the second protecting portion are apart from each other.

4. The ozone generating device according to claim 3, wherein the first protecting portion and the second protecting portion include openings corresponding to a tube diameter of the arc tube.

5. The ozone generating device according to claim 4, wherein a material is provided between one of the openings and the arc tube.

6. The ozone generating device according to claim 4, wherein a tapered portion is provided around the opening of the first protecting portion and around the opening of the second protecting portion.

7. The ozone generating device according to claim 3, further comprising:

a connecting portion that connects the first protecting portion with the second protecting portion, wherein the first protecting portion, the connecting portion, and the second protecting portion are provided integrally as the casing.

8. The ozone generating device according to claim 7, wherein the arc tube and the connecting portion are apart from each other.

9. The ozone generating device according to claim 3, wherein a material is provided between an end surface of the arc tube and an inner wall of the first protecting portion facing against the end surface of the arc tube, and between the end surface of the arc tube and the inner wall of the second protecting portion facing against the end surface of the arc tube, the material preventing light emitted from the end surface of the arc tube from reaching the inner wall.

10. The ozone generating device according to claim 1, wherein the ozone generating device is for vehicle applications.

11. An air conditioning device, comprising:

a flow channel;

an evaporating device provided within the flow channel;

the ozone generating device provided within the flow channel, the ozone generating device being according to claim 1; and an air blower provided on an upstream side of the evaporating device.

12. The air conditioning device according to claim 11, wherein the ozone generating device is positioned such that the tube-axial direction of the arc tube and an air-blowing direction intersect each other.

13. A vehicle, comprising:

the air conditioning device according to claim 11.

14. The vehicle according to claim 13, wherein the ozone generating device is positioned such that a direction perpendicular to a floor surface of the vehicle matches the tube-axial direction of the arc tube.

* * * * *